US011666525B2

(12) United States Patent
Florence et al.

(10) Patent No.: US 11,666,525 B2
(45) Date of Patent: Jun. 6, 2023

(54) TOPICAL SKIN CARE FORMULATIONS COMPRISING PLANT EXTRACTS

(71) Applicant: Mary Kay Inc., Addison, TX (US)

(72) Inventors: Tiffany Florence, Dallas, TX (US); David Gan, Southlake, TX (US); Michelle Hines, Hickory Creek, TX (US)

(73) Assignee: MARY KAY INC., Addison, TX (US)

( * ) Notice: Subject to any disclaimer, the term of this patent is extended or adjusted under 35 U.S.C. 154(b) by 78 days.

(21) Appl. No.: 17/186,481

(22) Filed: Feb. 26, 2021

(65) Prior Publication Data

US 2021/0177728 A1 Jun. 17, 2021

Related U.S. Application Data

(63) Continuation of application No. 16/373,366, filed on Apr. 2, 2019, now abandoned, which is a continuation of application No. 15/224,241, filed on Jul. 29, 2016, now Pat. No. 10,328,019, which is a continuation of application No. 14/517,540, filed on Oct. 17, 2014, now abandoned, which is a continuation of application No. 13/432,875, filed on Mar. 28, 2012, now Pat. No. 8,883,224.

(60) Provisional application No. 61/468,437, filed on Mar. 28, 2011.

(51) Int. Cl.

| A61K 8/9767 | (2017.01) |
| A61K 9/00 | (2006.01) |
| A61K 9/06 | (2006.01) |
| A61K 9/107 | (2006.01) |
| A61K 36/704 | (2006.01) |
| A61Q 19/02 | (2006.01) |
| A61K 8/9778 | (2017.01) |
| A61K 8/9789 | (2017.01) |
| A61K 8/9794 | (2017.01) |
| A61K 36/355 | (2006.01) |
| A61K 8/34 | (2006.01) |
| A61K 8/37 | (2006.01) |
| A61K 8/86 | (2006.01) |
| A61Q 19/00 | (2006.01) |
| A61Q 19/10 | (2006.01) |
| A61K 8/06 | (2006.01) |
| A61Q 19/08 | (2006.01) |
| A61K 47/10 | (2017.01) |
| A61K 47/12 | (2006.01) |
| A61K 47/14 | (2017.01) |
| A61K 47/36 | (2006.01) |

(52) U.S. Cl.
CPC ............ *A61K 8/9767* (2017.08); *A61K 8/062* (2013.01); *A61K 8/345* (2013.01); *A61K 8/375* (2013.01); *A61K 8/86* (2013.01); *A61K 8/9778* (2017.08); *A61K 8/9789* (2017.08); *A61K 8/9794* (2017.08); *A61K 9/0014* (2013.01); *A61K 9/06* (2013.01); *A61K 9/107* (2013.01); *A61K 36/355* (2013.01); *A61K 36/704* (2013.01); *A61Q 19/00* (2013.01); *A61Q 19/007* (2013.01); *A61Q 19/02* (2013.01); *A61Q 19/08* (2013.01); *A61Q 19/10* (2013.01); *A61K 47/10* (2013.01); *A61K 47/12* (2013.01); *A61K 47/14* (2013.01); *A61K 47/36* (2013.01); *A61K 2800/31* (2013.01); *A61K 2800/48* (2013.01); *A61K 2800/51* (2013.01); *A61K 2800/522* (2013.01); *A61K 2800/524* (2013.01); *A61K 2800/5922* (2013.01)

(58) Field of Classification Search
None
See application file for complete search history.

(56) References Cited

U.S. PATENT DOCUMENTS

| 5,958,437 | A | 9/1999 | Zaveri |
| 7,572,933 | B2 | 8/2009 | Gupta |
| 8,142,819 | B2 | 3/2012 | Tripp et al. |
| 8,529,925 | B2 | 9/2013 | Alexiades-Armenakas |
| 2004/0052870 | A1 | 3/2004 | Obukowicz et al. |
| 2004/0086580 | A1 | 5/2004 | Tripp et al. |
| 2004/0220137 | A1 | 11/2004 | Sauermann |
| 2005/0129780 | A1 | 6/2005 | Holcomb-Halstead et al. |
| 2006/0093571 | A1 | 5/2006 | Glinski |
| 2006/0142382 | A1 | 6/2006 | Morimoto et al. |
| 2006/0147397 | A1 | 7/2006 | Uehara et al. |
| 2006/0182798 | A1 | 8/2006 | Shimokawa et al. |
| 2007/0041993 | A1 | 2/2007 | Holcomb-Halstead et al. |

(Continued)

FOREIGN PATENT DOCUMENTS

| CN | 1201681 | 12/1998 |
| CN | 1371705 | 10/2002 |

(Continued)

OTHER PUBLICATIONS

"Sequoia.sempervirens" article (https://en.wikipedia.org/wiki/Sequoia_sempervirens)—accessed Sep. 2022.*

(Continued)

*Primary Examiner* — Susan Hoffman
(74) *Attorney, Agent, or Firm* — Norton Rose Fulbright US LLP

(57) ABSTRACT

A method for treating skin of a person is disclosed. The method can include topically applying to the skin of the person a composition comprising an effective amount of an aqueous, alcoholic, or aqueous-alcoholic extract from *Sequoia sempervirens, Geranium* oil, panthenol, citric acid, and glycerin, wherein the composition increases antioxidant activity in the skin and/or increases skin moisture content.

22 Claims, 1 Drawing Sheet

(56) References Cited

U.S. PATENT DOCUMENTS

| | | | |
|---|---|---|---|
| 2007/0166275 A1* | 7/2007 | Gan | A61K 8/9789 424/735 |
| 2008/0299159 A1 | 12/2008 | Aimi et al. | |
| 2009/0074691 A1 | 3/2009 | Gupta | |
| 2009/0104174 A1 | 4/2009 | Smith | |
| 2009/0104295 A1 | 4/2009 | Kohno | |
| 2011/0052731 A1 | 3/2011 | Park et al. | |
| 2011/0124542 A1 | 5/2011 | Sartingen | |
| 2011/0189322 A1 | 8/2011 | Florence et al. | |
| 2012/0058071 A1 | 3/2012 | Gross et al. | |
| 2012/0093755 A1 | 4/2012 | Humphreys et al. | |

FOREIGN PATENT DOCUMENTS

| | | | |
|---|---|---|---|
| CN | 1454630 | 11/2003 | |
| CN | 1985961 | 6/2007 | |
| CN | 101166506 | 4/2008 | |
| CN | 20091157404 | 7/2009 | |
| CN | 101547609 | 9/2009 | |
| CN | 102647920 | 8/2012 | |
| DE | 102009001483 | 1/2010 | |
| EP | 2145615 | 1/2010 | |
| JP | H03190809 | 8/1991 | |
| JP | H11193207 | 7/1999 | |
| JP | 2000169329 | 6/2000 | |
| JP | 2001-220313 | 8/2001 | |
| JP | 2003238345 | 8/2003 | |
| JP | 2004051568 | 2/2004 | |
| JP | 2004-083476 | 3/2004 | |
| JP | 2005-330286 | 12/2005 | |
| JP | 2007084448 | 4/2007 | |
| KR | 20050070732 | 8/2005 | |
| KR | 2007016002 | 2/2007 | |
| KR | 10-0780893 | 11/2007 | |
| KR | 10-0877188 | 1/2009 | |
| KR | 20090092095 | 8/2009 | |
| KR | 2010-0042090 | 4/2010 | |
| KR | 10-2011-0001538 | 1/2011 | |
| KR | 101082272 | 11/2011 | |
| WO | WO 2005/000262 | 1/2005 | |
| WO | WO 2009/067095 | 5/2009 | |
| WO | WO-2009107984 A2 * | 9/2009 | A61K 8/97 |
| WO | WO 2010/011997 | 1/2010 | |
| WO | WO 2012/105823 | 8/2012 | |

OTHER PUBLICATIONS

Corsetti et al., "Topical application of dressing with amino acids improves cutaneous wound healing in aged rats" *Acta histochemical* 2010, 112, 497-507.

Office Action issued in Corresponding Korean Application No. 10-2020-7028282, dated Jul. 6, 2021 (English Translation provided).

Patil et al., "Traditional uses of plants for wound healing in the Sangli district, Maharashtra" *International Journal of PharmTech Research* 2009, 1(3), 876-878.

Pillai et al., "Anti-Wrinkle Therapy: Significant New Findings in the Non-Invasive Cosmetic Treatment of Skin Wrinkles with Beta-Glucan" *IFSCC* 2005, 8(1), 2-6.

"Xinhua Outline of Materia Medica." Institute of Botany Jiangsu Province and Chinese Academy of Science, etc., the first edition, Shanghai Scientific & Technical Publishers, 1990, p. 246.

Office Action issued in Corresponding Chinese Application No. 201810431541.8, dated May 26, 2021 (English Translation provided).

Search Report issued in Corresponding Chinese Application No. 201810431541.8, dated May 20, 2021 (English Translation provided).

Atta & Alkofahi, "Anti-nociceptive and anti-inflammatory effects of some Jordanian medicinal plant extracts" Journal of Ethnopharmacology, 1998, 60:117-124.

International Preliminary Report on Patentability issued in International Patent Application No. PCT/US2012/030936, dated Oct. 10, 2013.

Lei et al., "Effect of traditional Chinese medicines on melanin biosynthesis I. Inhibitory actions of ethanolic extracts of 82 different Chinese crude medicines on tyrosinase activity" *Zhongcaoyao* 1999, 30(5), 336-339 (English Abstract).

Liao et al., "Effects of Elaeagnus bockii Diels polysaccharide on the small intestine of mice after whole body irradiation with 60Coy ray", World Chinese Journal of Digestology, 15/13: 1541-1544, May 2007.

Office Action issued in Corresponding Korean Application No. 10-2020-7028282, dated Dec. 3, 2020 (English Translation provided).

Office Action issued in corresponding Korean Patent Application No. 2018-7012165, dated Feb. 18, 2019 (Machine Translation).

Official Communication issued in Chinese Application No. 2012800204968 dated Apr. 21, 2015.

PCT International Search Report and Written Opinion issued in International Patent Application No. PCT/US2012/030936, dated Oct. 29, 2012.

Sonika et al., "Comparative Studies on Anti-Inflammatory Activity of Coriandrum Sativum, Datura Stramonium and Azadirachta Indica" *Asian J. Exp. Biol. Sci.* 2010, 1(1), 151-154.

Yang et al., "Regulatory Effects of Gamisamul-tang on Atopic Dermatitis Induced in the NC/Nga Mice", Korean Journal Oriental Physiology & Pathology, vol. 20, No. 4, pp. 1036-1043, Aug. 25, 2006.

Office Action issued in Corresponding Korean Application No. 10-2022-7013653, dated Jun. 26, 2022 (English Translation provided).

Wojdylo et al., "Sprouts vs. Microgreens as Novel Functional Foods: Variation of Nutritional and Phytochemical Profiles and Their In Vitro Bioactive Properties," Molecules 2020, 25, 4648, 19 pages.

Bowman et al., "The Benefits of Chlorophyll," https://www.healthline.com/health/liquid-chlorophyll-benefits-risks, © 2005-2022, downloaded Dec. 27, 2022.

* cited by examiner

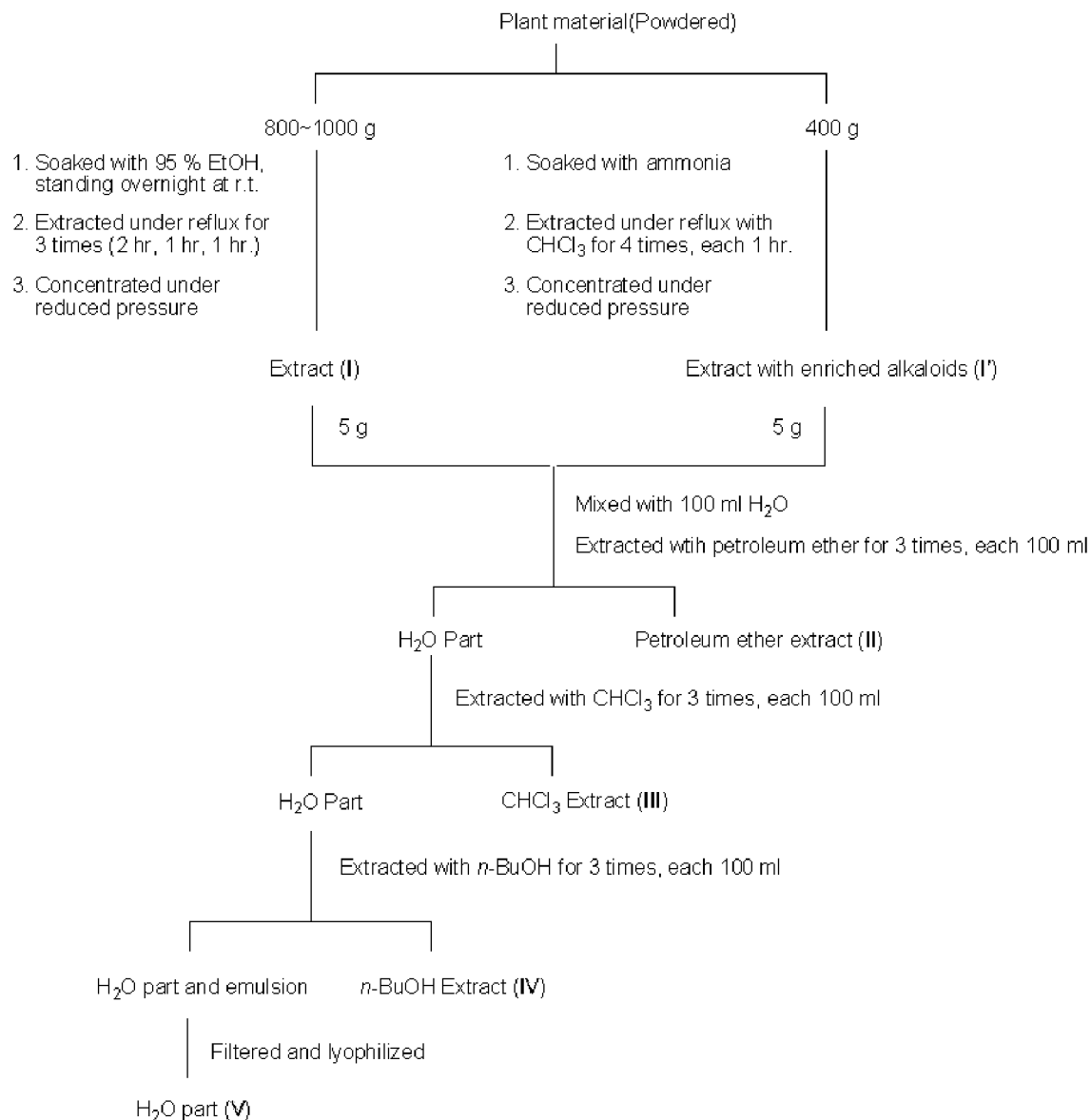

TOPICAL SKIN CARE FORMULATIONS COMPRISING PLANT EXTRACTS

CROSS REFERENCE TO RELATED APPLICATIONS

This application is a continuation of U.S. application Ser. No. 16/373,366 (now abandoned) filed Apr. 2, 2019, which is a continuation of U.S. application Ser. No. 15/224,241 (U.S. Pat. No. 10,328,019) filed Jul. 29, 2016, which is a continuation of U.S. application Ser. No. 14/517,540 (now abandoned) filed Oct. 17, 2014, which is a continuation of U.S. application Ser. No. 13/432,875 (U.S. Pat. No. 8,883,224), filed Mar. 28, 2012, which claims the benefit of U.S. Provisional Application No. 61/468,437, filed Mar. 28, 2011. The contents of the referenced applications are incorporated into the present application by reference.

BACKGROUND OF THE INVENTION

A. Field of the Invention

The present invention relates generally to compositions that include one or any combination of plants or extracts thereof selected from the group consisting of: *Oenothera rosea, Salvia plebeian, Alternanthera philoxeroides, Pyrus pyrifolia, Datura stramonium, Picris hieracioides* ssp. *Japonica, Phoebe neurantha, Acanthopanax gracilistylus, Osmanthus fragrans, Michelia chapensis, Rhododendron spinuliferum, Dendrobenthamia capitata, Ficus microcarpa, Vitex negundo, Sequoia sempervirens, Hypericum forrestii, Ficus pumila, Cercis chinensis, Rhododendron decorum, Ficus retusa* ssp. *nitida, Berchemia polyphylla* var. *leioclada, Elaeocarpus decipiens, Quercus variabilis, Prunus serrulata, Melastoma normale, Lycium chinensis, Chamaecyparis pisifera, Millettia dielsiana, Plumbago auriculata, Nandina domestica, Smilax bockii, Schima wallichii, Carissa spinarum, Wisteria floribunda, Schima argentea, Acacia decurrens* var. *dealbata, Viburnum ichangense, Conyza sumatrensis, Lantana camara, Euonymus bungeanus, Loropetalum chinensis* var. *rubrum, Jasminum mesnyi, Stellaria saxatilis, Elscholtzia cypriani, Daucus carota, Bougainvillea glabra, Serissa serissoides, Antidesma acidum, Sargentodoxa cuneata, Ajuga forrestii, Terminalia chebula, Paederia scandens, Lonicera japonica, Achyranthes bidentata, Hedera nepalensis, Canna chinensis, Ephedra sinica, Dichlrocephala auriculata, Prunus mume* var. *viridicalyx, Castanea molissima, Elaeagnus bockii, Parkia biglobosa, Cinnamomum parthenoxylon, Euphorbia esula, Sauropus androgynus, Chamaecrista mimosoides, Crotolaria zanzibarica, Castanopsis eyrei, Girardinia palmate, Phoenix roebelenii, Vinca major, Swertia macrosperma, Onosma paniculatum, Polygonum multiflorum, Gerbera jamesonii, Astragalus membranaceus, Duranta repens, Callicarpa macrophylla, Livistona chinensis, Incarvillea arguta, Lepidium virginicum, Fagopyrum cymosum, Quercus rehderiana, Cunninghamia lanceolata,* and *Deutzia glomeruliflora*. The compositions can be formulated as topical skin compositions, edible compositions, injectable compositions, oral compositions, hair care compositions, etc. In particular embodiments, any one of the following can be used or any combination thereof: *Lonicera japonica* extract, *Polygonum multiflorum* extract, and/or *Astragalus membranaceus* extract (combinations include *Lonicera japonica* extract with *Polygonum multiflorum* extract or *Lonicera japonica* extract with *Astragalus membranaceus* or *Polygonum multiflorum* extract with *Astragalus membranaceus* extract or *Lonicera japonica* extract, *Polygonum multiflorum* extract, and *Astragalus membranaceus* extract. In other instances, the following combination can be used: *Loropetalum chinensis* var. *rubrum* extract with *Ajuga forrestii* extract; *Loropetalum chinensis* var. *rubrum* extract with *Ephedra sinica* extract; *Ajuga forrestii* extract with *Ephedra sinica* extract; and *Loropetalum chinensis* var. *rubrum* extract, *Ephedra sinica* extract, and *Ajuga forrestii* extract.

B. Description of Related Art

Ageing, chronic exposure to adverse environmental factors, malnutrition, fatigue, etc., can change the visual appearance, physical properties, or physiological functions of skin in ways that are considered visually undesirable. The most notable and obvious changes include the development of fine lines and wrinkles, loss of elasticity, increased sagging, loss of firmness, loss of color evenness or tone, coarse surface texture, and mottled pigmentation. Less obvious, but measurable changes which occur as skin ages or endures chronic environmental insult include a general reduction in cellular and tissue vitality, reduction in cell replication rates, reduced cutaneous blood flow, reduced moisture content, accumulated errors in structure and function, alterations in the normal regulation of common biochemical pathways, and a reduction in the skin's ability to remodel and repair itself. Many of the alterations in appearance and function of the skin are caused by changes in the outer epidermal layer of the skin, while others are caused by changes in the lower dermis.

Previous attempts to improve the visual appearance of skin with known skin active-ingredients have been shown to have various drawbacks such as skin irritation and prolonged recovery periods.

SUMMARY OF THE INVENTION

The inventors discovered that a wide variety of plants, plant parts, and extracts thereof have therapeutic benefits. These plants and extracts thereof are from *Oenothera rosea, Salvia plebeian, Alternanthera philoxeroides, Pyrus pyrifolia, Datura stramonium, Picris hieracioides* ssp. *Japonica, Phoebe neurantha, Acanthopanax gracilistylus, Osmanthus fragrans, Michelia chapensis, Rhododendron spinuliferum, Dendrobenthamia capitata, Ficus microcarpa, Vitex negundo, Sequoia sempervirens, Hypericum forrestii, Ficus pumila, Cercis chinensis, Rhododendron decorum, Ficus retusa* ssp. *nitida, Berchemia polyphylla* var. *leioclada, Elaeocarpus decipiens, Quercus variabilis, Prunus serrulata, Melastoma normale, Lycium chinensis, Chamaecyparis pisifera, Millettia dielsiana, Plumbago auriculata, Nandina domestica, Smilax bockii, Schima wallichii, Carissa spinarum, Wisteria floribunda, Schima argentea, Acacia decurrens* var. *dealbata, Viburnum ichangense, Conyza sumatrensis, Lantana camara, Euonymus bungeanus, Loropetalum chinensis* var. *rubrum, Jasminum mesnyi, Stellaria saxatilis, Elscholtzia cypriani, Daucus carota, Bougainvillea glabra, Serissa serissoides, Antidesma acidum, Sargentodoxa cuneata, Ajuga forrestii, Terminalia chebula, Paederia scandens, Lonicera japonica, Achyranthes bidentata, Hedera nepalensis, Canna chinensis, Ephedra sinica, Dichlrocephala auriculata, Prunus mume* var. *viridicalyx, Castanea molissima, Elaeagnus bockii, Parkia biglobosa, Cinnamomum parthenoxylon, Euphorbia esula, Sauropus androgynus, Chamaecrista mimosoides, Crotolaria zanzibarica, Castanopsis eyrei, Girardinia palmate, Phoenix roebelenii,*

*Vinca major, Swertia macrosperma, Onosma paniculatum, Polygonum multiflorum, Gerbera jamesonii, Astragalus membranaceus, Duranta repens, Callicarpa macrophylla, Livistona chinensis, Incarvillea arguta, Lepidium virginicum, Fagopyrum cymosum, Quercus rehderiana, Cunninghamia lanceolata,* and/or *Deutzia glomeruliflora.* In particular aspects, compositions of the present invention can include any one of, any combination of, all of, or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, or 85 of said plants, plant parts, and/or extracts thereof. In particular instances, the combination of *Loropetalum chinensis* var. *rubrum* and *Ajuga forrestii* extracts was found to work especially well to provide skin with protection from oxidative events (e.g., oxidation caused by reaction oxidative species or environmental conditions or sun exposure) as well as inhibit TNF-α activity (which can reduce skin inflammation, calm or soothe skin, and treat erythemic skin), inhibit tyrosinae activity (which can be used to lighten skin, even skin tone, and treat hyperpigmentation, sun spots, or melasma), and increase or activate collagen synthesis in the skin (which can be used to rebuild the skin matrix, increase collagen within skin, and treat fine lines or wrinkles). In some instances, the addition of *Ephedra sinica* extract can also be used to further supplement the inhibition of Tyrosinase activity in skin. Alternatively, and in some instances, the combination of *Loropetalum chinensis* var. *rubrum* with *Ephedra sinica* extract was found to work well together in inhibiting tyrosinase activity in that the combination can produce a synergistic effect. In even other embodiments, a combination of *Ajuga forrestii* extract with *Ephedra sinica* extract can be used to provide skin with protection from oxidative events (e.g., oxidation caused by reaction oxidative species or environmental conditions or sun exposure) as well as inhibit TNF-α activity (which can reduce skin inflammation, calm or soothe skin, and treat erythemic skin), inhibit tyrosinae activity (which can be used to lighten skin, even skin tone, and treat hyperpigmentation, sun spots, or melasma), and increase or activate collagen synthesis in the skin (which can be used to rebuild the skin matrix, increase collagen within skin, and treat fine lines or wrinkles). In particular instances, the extracts can be from the whole plant and can be aqueous extracts. However, it is contemplated that in addition to the whole plant, part of the plant (e.g., root, bark, sap, stem, leaf, flower, seed, leaf, stem, root, flower, seed, sap, bark, etc.) can be used such that one portion of the plant is used at the exclusion of the other portions of the plant to produce the extract. As noted above, the extract can be an aqueous extract but can also be a non-aqueous extract. The extract can be extracted with alcohol (e.g., methanol, ethanol propanol, butanol, etc.), glycols (e.g., butylene glycol, propylene glycol, etc.), oils, water, etc. The extracts can be included in compositions such as topical skin compositions, edible compositions, injectable compositions, oral compositions, pharmaceutical compositions, hair care compositions, etc. The composition can include 0.0001% to 20% by weight of said plant, plant part, and/or extract thereof (or 0.001, 0.01, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 30, 40, 50, 60, 70, 80, 90, 99%, or more or any integer or range therein).

In one embodiment, there is disclosed a topical skin composition comprising a TNF-α inhibitor, wherein said inhibitor is an aqueous extract from the whole plant (or any part thereof) of *Polygonum multiflorum* and/or an antioxidant and a tyrosinase inhibitor, wherein said antioxidant and tyrosinase inhibitor is an aqueous extract from the whole plant (or any part thereof) of *Lonicera japonica* and a dermatologically acceptable carrier, wherein the composition comprises at least 50% by weight of water. In certain aspect, the composition can include at 30 to 95% by weight of water, 45 to 95% by weight of water, 55 to 95% by weight of water, 65 to 95% by weight of water 75 to 95% by weight of water or 85 to 95% by weight of water. In certain aspects, the composition can include 0.001 to 5% by weight of *Polygonum multiflorum* extract and/or 0.001 to 5% by weight of *Lonicera japonica* extract and said amounts can be greater if desired (e.g., 6, 7, 8, 9, 10, 15, 20% by weight or more). The composition can be a lotion, cream, gel, serum, or emulsion. The composition can include a moisturization agent, an antioxidant, a structuring or thickening agent, and an emulsifier, non-limiting examples of said ingredients are provided below in this specification. The composition can further include a silicone containing compound and/or a sunscreen agent, non-limiting examples of said ingredients are provided below in this specification. In some instances, the composition can further include an aqueous extract from the whole plant (or any part thereof) of *Astragalus membranaceus*. The composition can be formulated as a cosmetic product, non-limiting examples of which can be a cleanser product, a toner product, a moisturizer product, or a mask product. Also disclosed is a method of using said composition to treat skin in need thereof. The composition is capable of inhibiting/reducing TNF-α activity and tyrosinase activity in said skin. The composition is also capable of preventing oxidative damage in skin/skin cells. The composition can be applied to inflamed skin (e.g., sensitive skin, erythemic skin, etc.). The composition can be applied to hyperpigmented skin, a sunspot, a liver spot, an age spot, or melasmic skin. The composition can be applied to skin having or diagnosed with uneven skin tone.

In another particular embodiment, there is disclosed a topical skin composition comprising an extract from the whole plant (or any part thereof) of *Loropetalum chinensis* var. *rubrum* and/or an extract from the whole plant of *Ajuga forrestii* and a dermatologically acceptable carrier. The composition can include at 30 to 95% by weight of water, 45 to 95% by weight of water, 55 to 95% by weight of water, 65 to 95% by weight of water 75 to 95% by weight of water or 85 to 95% by weight of water. In certain aspects, the composition can include 0.001 to 5% by weight of *Loropetalum chinensis* var. *rubrum* extract and/or 0.001 to 5% by weight of *Ajuga forrestii* extract and said amounts can be greater if desired (e.g., 6, 7, 8, 9, 10, 15, 20% by weight or more). The extracts can be aqueous extracts. The composition can be a lotion, cream, gel, serum, emulsion, in powdered form, or a product such as a cleanser, toner, moisturizer, mask, or sunscreen. The composition can include a moisturization agent, an antioxidant, a structuring or thickening agent, and an emulsifier, non-limiting examples of each of these ingredients are provided below in the specification. The composition can further include a silicone containing compound and/or a sunscreen agent, non-limiting examples of which are also provided below in the specification. In some aspects, the composition can further include an extract from the whole plant (or any part thereof) of *ephedra sinica*. Also contemplated is a method of treating skin comprising topically applying this composition to skin in need thereof, wherein topical application of said composition treats said skin. The composition can inhibit TNF-α activity in said skin. The composition can be applied to inflamed skin, erythemic skin, sensitive skin, dry skin, flaky skin, or itchy skin. The composition can stimulate collagen synthesis in said skin. The composition can be applied to a fine line or wrinkle, sagging skin, or loose skin, or skin having pits or nodules. The composition can reduce oxidative damage in skin cells. The composition can inhibit tyrosinase activity in said skin. The composition can be applied to hyperpigmented skin, a sunspot, an age spot, a liver spot, or melasmic skin. Also contemplated is a method inhibiting tyrosinase activity in skin comprising topically applying to skin in need thereof a composition comprising an extract from the whole plant (or any part thereof) of *Loropetalum chinensis* var. *rubrum* and/or an extract from the whole plant (or any part thereof) of *Ephedra sinica*, wherein topical application of said composition inhibits tyrosinase activity in said skin. The composition can be applied to hyperpigmented skin, melasmic skin, a sunspot or age spot on said skin, or skin having an uneven skin tone.

In particular aspects, the compositions of the present invention are formulated as topical skin composition. The composition can have a dermatologically acceptable vehicle or carrier for the plant, plant part, or extract thereof. The composition can further include a moisturizing agent or a humectant, a surfactant, a silicone containing compounds, a UV agent, an oil, and/or other ingredients identified in this specification or those known in the art. The composition can be a lotion, cream, gel, serum, emulsion (e.g., oil-in-water, water-in-oil, silicone-in-water, water-in-silicone, water-in-oil-in-water, oil-in-water, oil-in-water-in-oil, oil-in-water-in-silicone, etc.), solutions (e.g., aqueous or hydro-alcoholic solutions), anhydrous bases (e.g., lipstick or a powder), ointments, milk, paste, aerosol, solid forms, eye jellies, etc. The composition can be in powdered form (e.g., dried, lyophilized, particulate, etc.). The composition can be formulated for topical skin application at least 1, 2, 3, 4, 5, 6, 7, or more times a day during use. In other aspects of the present invention, compositions can be storage stable or color stable, or both. It is also contemplated that the viscosity of the composition can be selected to achieve a desired result, e.g., depending on the type of composition desired, the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, cps, etc., as measured on a Brookfield Viscometer using a TC spindle at 2.5 rpm at 25° C.).

The compositions of the present invention can also be modified to have a desired oxygen radical absorbance capacity (ORAC) value. In certain non-limiting aspects, the compositions of the present invention or the plant, plant parts, or extracts thereof identified throughout this specification can be modified to have an ORAC value per mg of at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 70, 80, 90, 95, 100, 200, 300, 400, 500, 600, 700, 800, 900, 1000, 2000, 3000, 4000, 5000, 6000, 7000, 8000, 9000, 10000, 15000, 20000, 30000, 50000, 100000 or more or any range derivable therein.

The compositions in non-limiting aspects can have a pH of about 6 to about 9. In other aspects, the pH can be 1, 2, 3, 4, 5, 6, 7, 8, 9, 10, 11, 12, 13, or 14. The compositions can include a triglyceride. Non-limiting examples include small, medium, and large chain triglycerides. In certain aspects, the triglyceride is a medium chain triglyceride (e.g., caprylic capric triglyceride). The compositions can also include preservatives. Non-limiting examples of preservatives include methylparaben, propylparaben, or a mixture of methylparaben and propylparaben.

Compositions of the present invention can have UVA and UVB absorption properties. The compositions can have an sun protection factor (SPF) of 2, 3, 4, 5, 6, 7, 8, 9, 10, 11, 12, 13, 14, 15, 20, 25, 30, 35, 40, 45, 50, 55, 60, or more, or any integer or derivative therein. The compositions can be sunscreen lotions, sprays, or creams.

The compositions of the present invention can also include any one of, any combination of, or all of the following additional ingredients: water, a chelating agent, a moisturizing agent, a preservative, a thickening agent, a silicone containing compound, an essential oil, a structuring agent, a vitamin, a pharmaceutical ingredient, or an antioxidant, or any combination of such ingredients or mixtures of such ingredients. In certain aspects, the composition can include at least two, three, four, five, six, seven, eight, nine, ten, or all of these additional ingredients identified in the previous sentence. Non-limiting examples of these additional ingredients are identified throughout this specification and are incorporated into this section by reference. The amounts of such ingredients can range from 0.0001% to 99.9% by weight or volume of the composition, or any integer or range in between as disclosed in other sections of this specification, which are incorporated into this paragraph by reference.

In another embodiment, there is disclosed a topical skin care composition that includes an one of or combination of the aforementioned plants, plant parts, and/or extracts thereof in combination with any one of, any combination of, or all of the following ingredients: water; glycerin; butylene glycol; propylene glycol; phenoxyethanol; a chelating agent (e.g., EDTA, disodium EDTA, trisodium EDTA, EGTA, disodium EGTA, trisodium EGTA, citric acid, phosphoric acid, succinic acid, etc.); steareth-20; chlorhexidine diglunonate; potassium sorbate; and/or a preservative (e.g., methylparaben, propylparaben, butylparaben, ethylparaben, isobutylparaben, etc.). In particular aspects, the composition can further include any one of, any combination of, or all of the following additional ingredients: alcohol; denatured alcohol; glyceryl stearate; dimethicone; PEG-100 stearate; capryl glycol; triethanolamine; maltodextrin; sorbic acid; ethylene brassylate; methyl linalool; isobutyl methyl tetrahydropyranol; ethylhexylglycerin; and/or hexylene glycol. The concentrations of these ingredients can range from 0.00001 to 99% by weight or volume of the composition or any integer or range derivable therein as explained in other portions of this specification which are incorporated into this paragraph by reference. In particular aspects, the concentration of water can be at least 35% to 80% by weight of water.

In another embodiment, there is disclosed a topical skin care composition that includes an one of or combination of the aforementioned plants, plant parts, and/or extracts thereof in combination with any one of, any combination of, or all of the following ingredients: water; dimethicone; triethanolamine; phenonip; betaine; a chelating agent (e.g., EDTA, disodium EDTA, trisodium EDTA, EGTA, disodium EGTA, trisodium EGTA, citric acid, phosphoric acid, succinic acid, etc.); tocopheryl acetate; and/or prodew 400. In particular aspects, the composition can further include any one of, any combination of, or all of the following additional ingredients: propylene glycol; isododecane; polyacrylamide/C13-C14 isoparaffin/laureth 7 mixture; PEG-12 dimethicone; and/or ethylhexyl palmitate. The concentrations of these ingredients can range from 0.00001 to 99% by weight or volume of the composition or any integer or range derivable therein as explained in other portions of this specification which are incorporated into this paragraph by reference. In particular aspects, the concentration of water can be at least 35% to 80% by weight of water.

In another embodiment, there is disclosed a topical skin care composition that includes an one of or combination of the aforementioned plants, plant parts, and/or extracts thereof in combination with any one of, any combination of, or all of the following ingredients: water; glycerin; pentylene glycol; capryl glycol; disodium EDTA; capric/caprylic triglyceride; shea butter; squalane; cetyl alcohol; dimethicone; ceramide II; stearic acid; a mixture of glyceryl stearate and PEG 100 stearate; or a mixture of acrylamide/acryloyl dimethyl taurate copolymer, isohexadecane, and polysorbate 80. The concentrations of these ingredients can range from 0.00001 to 99% by weight or volume of the composition or any integer or range derivable therein as explained in other portions of this specification which are incorporated into this paragraph by reference. In particular aspects, the concentration of water can be at least 35% to 80% by weight of water. The ratio of water to glycerin can be from about 7:1 to 9:1 based on the total weight of the composition. The ratio of glycerin to pentylene glycol can be from about 1:1 to about 2:1 based on the total weight of the composition.

In another embodiment, there is disclosed a topical skin care composition that includes any one of or combination of the aforementioned plants, plant parts, and/or extracts thereof in combination with any one of, any combination of, or all of the following ingredients: water; glycerin; capryl glycol; capryl glycol; disodium EDTA; petrolatum; squalane; cetyl alcohol; a mixture of glyceryl stearate and PEG 100 stearate; dimethicone; or a mixture of acrylamide/acryloyl dimethyl taurate copolymer, isohexadecane, and polysorbate 80. The concentrations of these ingredients can range from 0.00001 to 99% by weight or volume of the composition or any integer or range derivable therein as explained in other portions of this specification which are incorporated into this paragraph by reference. In particular aspects, the concentration of water can be at least 35% to 80% by weight of water. The ratio of water to glycerin can be from about 12:1 to 16:1 based on the total weight of the composition. The ratio of glycerin to pentylene glycol can be from about 0.5:1 to about 1.5:1 based on the total weight of the composition.

In another embodiment, there is disclosed a topical skin care composition that includes any one of or combination of the aforementioned plants, plant parts, and/or extracts thereof in combination with any one of, any combination of, or all of the following ingredients: water; xanthan gum; disodium EDTA; pentylene glycol; capryl glycol; acrylate C10-30 acrylate cross polymer; triethanolamine; PVP/hexadecene copolymer; C12-15 alkyl benzoate; sorbitan isostearate; or a sunscreen agent. The concentrations of these ingredients can range from 0.00001 to 99% by weight or volume of the composition or any integer or range derivable therein as explained in other portions of this specification which are incorporated into this paragraph by reference. In particular aspects, the concentration of water can be at least 35% to 80% by weight of water. The ratio of water to C12-15 alkyl benzoate can be from about 2:1 to 3:1 based on the total weight of the composition. The ratio of water to pentylene glycol can be from about 9:1 to about 11:1 based on the total weight of the composition.

In another embodiment, there is disclosed a topical skin care composition that includes any one of or combination of the aforementioned plants, plant parts, and/or extracts thereof in combination with any one of, any combination of, or all of the following ingredients: water; disodium EDTA; citric acid; pentylene glycol; capryl glycol; sodium cocoamphodiacetate; or sodium methyl cocoyl taurate. The concentrations of these ingredients can range from 0.00001 to 99% by weight or volume of the composition or any integer or range derivable therein as explained in other portions of this specification which are incorporated into this paragraph by reference. In particular aspects, the concentration of water can be at least 35% to 80% by weight of water. The ratio of water to pentylene glycol can be from about 12:1 to 14:1 based on the total weight of the composition. The ratio of water to sodium cocoamphodiacetate can be from about 8:1 to about 11:1 based on the total weight of the composition. The ratio of water to sodium methyl cocoyl taurate can be from about 2:1 to about 4:1 based on the total weight of the composition. The ratio of sodium methyl cocoyl taurate to sodium cocoamphodiacetate can be from about 2:1 to about 4:1 based on the total weight of the composition.

Also disclosed is an extract from *Oenothera rosea, Salvia plebeian, Alternanthera philoxeroides, Pyrus pyrifolia, Datura stramonium, Picris hieracioides* ssp. *Japonica, Phoebe neurantha, Acanthopanax gracilistylus, Osmanthus fragrans, Michelia chapensis, Rhododendron spinuliferum, Dendrobenthamia capitata, Ficus microcarpa, Vitex negundo, Sequoia sempervirens, Hypericum forrestii, Ficus pumila, Cercis chinensis, Rhododendron decorum, Ficus retusa* ssp. *nitida, Berchemia polyphylla* var. *leioclada, Elaeocarpus decipiens, Quercus variabilis, Prunus serrulata, Melastoma normale, Lycium chinensis, Chamaecyparis pisifera, Millettia dielsiana, Plumbago auriculata, Nandina domestica, Smilax bockii, Schima wallichii, Carissa spinarum, Wisteria floribunda, Schima argentea, Acacia decurrens* var. *dealbata, Viburnum ichangense, Conyza sumatrensis, Lantana camara, Euonymus bungeanus, Loropetalum chinensis* var. *rubrum, Jasminum mesnyi, Stellaria saxatilis, Elscholtzia cypriani, Daucus carota, Bougainvillea glabra, Serissa serissoides, Antidesma acidum, Sargentodoxa cuneata, Ajuga forrestii, Terminalia chebula, Paederia scandens, Lonicera japonica, Achyranthes bidentata, Hedera nepalensis, Canna chinensis, Ephedra sinica, Dichlrocephala auriculata, Prunus mume* var. *viridicalyx, Castanea molissima, Elaeagnus bockii, Parkia biglobosa, cinnamomum parthenoxylon, Euphorbia esula, Sauropus androgynus, Chamaecrista mimosoides, Crotolaria zanzibarica, Castanopsis eyrei, Girardinia palmate, Phoenix roebelenii, Vinca major, Swertia macrosperma, Onosma paniculatum, Polygonum multiflorum, Gerbera jamesonii, Astragalus membranaceus, Duranta repens, Callicarpa macrophylla, Livistona chinensis, Incarvillea arguta, Lepidium virginicum, Fagopyrum cymosum, Quercus rehderiana, Cunninghamia lanceolata,* and/or *Deutzia glomeruliflora*. The extract can be from the whole plant or part of the plant (e.g., root, bark, sap, stem, leaf, flower, seed, leaf, stem, root, flower, seed, sap, bark, etc.), or mixtures from different parts of the plant. The extract can be an aqueous extract or a non-aqueous extract. The extract can be extracted with alcohol (e.g., methanol, ethanol propanol, butanol, etc.), glycols, oils, water, etc. The extracts can be included in a composition. The composition can include 0.01% to 20% by weight of said plant, plant part, and/or extract thereof (or 0.1, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 30, 40, 50, 60, 70, 80, 90, 99%, or more or any integer or range therein).

The composition can include any one of, any combination of, all of, or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, or 85 of said extracts. The plant part can be the whole plant or part of the plant (e.g., root, bark, sap, stem, leaf, flower, seed, leaf, stem, root, flower, seed, sap, bark, etc.). The extract can be from the whole plant or part of the plant (e.g., root, bark, sap, stem, leaf, flower, seed, leaf, stem, root, flower, seed, sap, bark, etc.). The extract can be an aqueous extract or a non-aqueous extract. The extract can be extracted with alcohol (e.g., methanol, ethanol propanol, butanol, etc.), glycols, oils, water, etc. The composition can take the form of a pill, liquid gel cap, tablet, or powder. The composition can be an injectable solution (e.g., for intravenous delivery). The composition can be in the form of a neutraceutical. The composition can be a topical skin composition. The composition can be in aerosolized form. The extract can be an aqueous or a non-aqueous extract. The aqueous extract can include an alcohol, a glycol, water and/or water. Non-aqueous extract can include a fat or an oil.

One aspect of the present invention concerns a method of treating or preventing a skin condition comprising topically applying any one of the compositions disclosed in this specification to skin having a skin condition. As noted throughout, the composition can include a plant, plant part, or extract thereof from *Oenothera rosea, Salvia plebeian, Alternanthera philoxeroides, Pyrus pyrifolia, Datura stramonium, Picris hieracioides* ssp. *Japonica, Phoebe neurantha, Acanthopanax gracilistylus, Osmanthus fragrans, Michelia chapensis, Rhododendron spinuliferum, Dendrobenthamia capitata, Ficus microcarpa, Vitex negundo, Sequoia sempervirens, Hypericum forrestii, Ficus pumila, Cercis chinensis, Rhododendron decorum, Ficus retusa* ssp. *nitida, Berchemia polyphylla* var. *leioclada, Elaeocarpus decipiens, Quercus variabilis, Prunus serrulata, Melastoma normale, Lycium chinensis, Chamaecyparis pisifera, Millettia dielsiana, Plumbago auriculata, Nandina domestica, Smilax bockii, Schima wallichii, Carissa spinarum, Wisteria floribunda, Schima argentea, Acacia decurrens* var. *dealbata, Viburnum ichangense, Conyza sumatrensis, Lantana camara, Euonymus bungeanus, Loropetalum chinensis* var. *rubrum, Jasminum mesnyi, Stellaria saxatilis, Elscholtzia cypriani, Daucus carota, Bougainvillea glabra, Serissa serissoides, Antidesma acidum, Sargentodoxa cuneata, Ajuga forrestii, Terminalia chebula, Paederia scandens, Lonicera japonica, Achyranthes bidentata, Hedera nepalensis, Canna chinensis, Ephedra sinica, Dichlrocephala auriculata, Prunus mume* var. *viridicalyx, Castanea molissima, Elaeagnus bockii, Parkia biglobosa, cinnamomum parthenoxylon, Euphorbia esula, Sauropus androgynus, Chamaecrista mimosoides, Crotolaria zanzibarica, Castanopsis eyrei, Girardinia palmate, Phoenix roebelenii, Vinca major, Swertia macrosperma, Onosma paniculatum, Polygonum multiflorum, Gerbera jamesonii, Astragalus membranaceus, Duranta repens, Callicarpa macrophylla, Livistona chinensis, Incarvillea arguta, Lepidium virginicum, Fagopyrum cymosum, Quercus rehderiana, Cunninghamia lanceolata,* and/or *Deutzia glomeruliflora.* The composition can include any one of, any combination of, all of, or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, or 85 of said plants, plant parts, and/or extracts thereof. The plant part can be the whole plant or part of the plant (e.g., root, bark, sap, stem, leaf, flower, seed, leaf, stem, root, flower, seed, sap, bark, etc.). The extract can be from the whole plant or part of the plant (e.g., root, bark, sap, stem, leaf, flower, seed, leaf, stem, root, flower, seed, sap, bark, etc.). The extract can be an aqueous extract or a non-aqueous extract. The extract can be extracted with alcohol (e.g., methanol, ethanol propanol, butanol, etc.), glycols, oils, water, etc. The composition can include a dermatoligically acceptable vehicle. Non-limiting examples of skin conditions that can be treated and/or prevented with the compositions of the present invention include dry skin, itchy skin, flaky skin, inflamed skin, erythemic skin, pain associated with erythemic skin, sensitive skin, pruritus, spider veins, lentigo, age spots, senile purpura, keratosis, melasma, blotches, fine lines or wrinkles, nodules, sun damaged skin, dermatitis (including, but not limited to seborrheic dermatitis, nummular dermatitis, contact dermatitis, atopic dermatitis, exfoliative dermatitis, perioral dermatitis, and stasis dermatitis), psoriasis, folliculitis, rosacea, acne, postules, nodules, whiteheads, blackheads, impetigo, erysipelas, erythrasma, eczema, sun burns, burned skin, open wounds, skin-inflammatory skin conditions, etc. In certain non-limiting aspects, the skin condition can be caused by exposure to UV light, age, irradiation, chronic sun exposure, environmental pollutants, air pollution, wind, cold, heat, chemicals, disease pathologies, smoking, or lack of nutrition. The skin can be facial skin or non-facial skin (e.g., arms, legs, hands, chest, back, feet, etc.). The method can further comprise identifying a person in need of skin treatment. The person can be a male or female. The age of the person can be at least 1, 2, 3, 4, 5, 6, 7, 8, 9, 10, 15, 20, 25, 30, 35, 40, 45, 50, 55, 60, 65, 70, 75, 80, 85, 90, 95, or more years old, or any range derivable therein. The method can also include topically applying an amount effective to: increase the stratum corneum turnover rate of the skin; increase collagen synthesis in fibroblasts; increase cellular anti-oxidant defense mechanisms (e.g., exogenous additions of anti-oxidants can bolster, replenish, or prevent the loss of cellular antioxidants such as catalase and glutathione in skin cells (e.g., keratinocytes, melanocytes, langerhans cells, etc.) which will reduce or prevent oxidative damage to the skin, cellular, proteins, and lipids); inhibit melanin production in melanocytes; reduce or prevent oxidative damage to skin (including reducing the amount lipid peroxides and/or protein oxidation in the skin).

In yet another embodiment, the extracts disclosed throughout this specification can be used treat skin conditions or diseases associated with oxidation of skin cells (e.g., extracts that have antioxidative properties), melanin production (e.g., extracts that have the ability to modify or otherwise inhibit melanin production in skin cells), tyrosinase activity (e.g., extracts that have the ability to modify or otherwise inhibit tyrosinase activity in skin cells), TNF-α activity (e.g., extracts that have the ability to modify or otherwise inhibit TNF-α activity), and collagen production (e.g., extracts that have the ability to modify or otherwise increase or stimulate collagen production). The data in the Examples and the information provided in the Detailed Description concerning the extracts provide information on the antioxidant, melanin inhibition, TNF-α inhibition, tyrosinase inhibition, and collagen production abilities of said extracts. In particular embodiments, extracts that have antioxidant properties can be used to treat, prevent, or reduce oxidative damage to skin cells from external environmental factors (e.g., pollution, sun, chemicals, etc.). Extracts having TNF-α inhibition properties can be used to reduce TNF-α activity in skin cells having increased TNF-α activity (e.g., inflamed skin, red skin, erythemic skin, sun burned skin, burned skin, or other skin-related diseases that are also inflammatory diseases). Extracts having melanin inhibition or tyrosinase inhibition properties can be used to reduce or otherwise prevent melanin or tyrosinase production or activity in skin cells, which can be used to treat hyperpigmented skin, uneven skin, melasmic skin, dark spots, aged spots, sun spots, blotchy skin, etc. Extracts having the ability to increase collagen production or promote collagen production in skin cells can be used to treat fine lines and wrinkles, sagging skin, loose skin, etc.

In one embodiment of the present invention there is disclosed a method of reducing the appearance of symptoms associated with erythema (e.g., erythemic skin, sensitive skin, inflamed skin) comprising topically applying any one of the compositions of the present invention to skin in need thereof. Erythema can be caused by skin sunburn, electrical treatments of skin, skin burns, contact allergies, systemic allergies, skin toxicity, exercise, insect stings, bacterial infection, viral infection, fungal infection, protozoa infection, massage, windburn, etc. As noted throughout, the composition can include a plant, plant part, or extract thereof from *Oenothera rosea, Salvia plebeian, Alternanthera philoxeroides, Pyrus pyrifolia, Datura stramonium, Picris hieracioides* ssp. *Japonica, Phoebe neurantha, Acanthopanax gracilistylus, Osmanthus fragrans, Michelia chapensis, Rhododendron spinuliferum, Dendrobenthamia capitata, Ficus microcarpa, Vitex negundo, Sequoia sempervirens, Hypericum forrestii, Ficus pumila, Cercis chinensis, Rhododendron decorum, Ficus retusa* ssp. *nitida, Berchemia polyphylla* var. *leioclada, Elaeocarpus decipiens, Quercus variabilis, Prunus serrulata, Melastoma normale, Lycium chinensis, Chamaecyparis pisifera, Millettia dielsiana, Plumbago auriculata, Nandina domestica, Smilax bockii, Schima wallichii, Carissa spinarum, Wisteria floribunda, Schima argentea, Acacia decurrens* var. *dealbata, Viburnum ichangense, Conyza sumatrensis, Lantana camara, Euonymus bungeanus, Loropetalum chinensis* var. *rubrum, Jasminum mesnyi, Stellaria saxatilis, Elscholtzia cypriani, Daucus carota, Bougainvillea glabra, Serissa serissoides, Antidesma acidum, Sargentodoxa cuneata, Ajuga forrestii, Terminalia chebula, Paederia scandens, Lonicera japonica, Achyranthes bidentata, Hedera nepalensis, Canna chinensis, Ephedra sinica, Dichlrocephala auriculata, Prunus mume* var. *viridicalyx, Castanea molissima, Elaeagnus bockii, Parkia biglobosa, cinnamomum parthenoxylon, Euphorbia esula, Sauropus androgynus, Chamaecrista mimosoides, Crotolaria zanzibarica, Castanopsis eyrei, Girardinia palmate, Phoenix roebelenii, Vinca major, Swertia macrosperma, Onosma paniculatum, Polygonum multiflorum, Gerbera jamesonii, Astragalus membranaceus, Duranta repens, Callicarpa macrophylla, Livistona chinensis, Incarvillea arguta, Lepidium virginicum, Fagopyrum cymosum, Quercus rehderiana, Cunninghamia lanceolata*, and/or *Deutzia glomeruliflora*. The composition can include any one of, any combination of, all of, or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, or 85 of said plants, plant parts, and/or extracts thereof. The plant part can be the whole plant or part of the plant (e.g., root, bark, sap, stem, leaf, flower, seed, leaf, stem, root, flower, seed, sap, bark, etc.). The extract can be from the whole plant or part of the plant (e.g., root, bark, sap, stem, leaf, flower, seed, leaf, stem, root, flower, seed, sap, bark, etc.). The extract can be an aqueous extract or a non-aqueous extract. The extract can be extracted with alcohol (e.g., methanol, ethanol propanol, butanol, etc.), glycols, oils, water, etc.

In still another aspect of the present invention there is disclosed a method of treating dry, flaky, or itchy skin or reducing the appearance of uneven skin tone comprising topically applying any one of the compositions disclosed in this specification to dry, flaky, or itchy skin or to skin having an uneven skin tone. As noted throughout, the composition can include a plant, plant part, or extract thereof from *Oenothera rosea, Salvia plebeian, Alternanthera philoxeroides, Pyrus pyrifolia, Datura stramonium, Picris hieracioides* ssp. *Japonica, Phoebe neurantha, Acanthopanax gracilistylus, Osmanthus fragrans, Michelia chapensis, Rhododendron spinuliferum, Dendrobenthamia capitata, Ficus microcarpa, Vitex negundo, Sequoia sempervirens, Hypericum forrestii, Ficus pumila, Cercis chinensis, Rhododendron decorum, Ficus retusa* ssp. *nitida, Berchemia polyphylla* var. *leioclada, Elaeocarpus decipiens, Quercus variabilis, Prunus serrulata, Melastoma normale, Lycium chinensis, Chamaecyparis pisifera, Millettia dielsiana, Plumbago auriculata, Nandina domestica, Smilax bockii, Schima wallichii, Carissa spinarum, Wisteria floribunda, Schima argentea, Acacia decurrens* var. *dealbata, Viburnum ichangense, Conyza sumatrensis, Lantana camara, Euonymus bungeanus, Loropetalum chinensis* var. *rubrum, Jasminum mesnyi, Stellaria saxatilis, Elscholtzia cypriani, Daucus carota, Bougainvillea glabra, Serissa serissoides, Antidesma acidum, Sargentodoxa cuneata, Ajuga forrestii, Terminalia chebula, Paederia scandens, Lonicera japonica, Achyranthes bidentata, Hedera nepalensis, Canna chinensis, Ephedra sinica, Dichlrocephala auriculata, Prunus mume* var. *viridicalyx, Castanea molissima, Elaeagnus bockii, Parkia biglobosa, cinnamomum parthenoxylon, Euphorbia esula, Sauropus androgynus, Chamaecrista mimosoides, Crotolaria zanzibarica, Castanopsis eyrei, Girardinia palmate, Phoenix roebelenii, Vinca major, Swertia macrosperma, Onosma paniculatum, Polygonum multiforum, Gerbera jamesonii, Astragalus membranaceus, Duranta repens, Callicarpa macrophylla, Livistona chinensis, Incarvillea arguta, Lepidium virginicum, Fagopyrum cymosum, Quercus rehderiana, Cunninghamia lanceolata*, and/or *Deutzia glomeruliflora*. The composition can include any one of, any combination of, all of, or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, or 85 of said plants, plant parts, and/or extracts thereof. The plant part can be the whole plant or part of the plant (e.g., root, bark, sap, stem, leaf, flower, seed, leaf, stem, root, flower, seed, sap, bark, etc.). The extract can be from the whole plant or part of the plant (e.g., root, bark, sap, stem, leaf, flower, seed, leaf, stem, root, flower, seed, sap, bark, etc.). The extract can be an aqueous extract or a non-aqueous extract. The extract can be extracted with alcohol (e.g., methanol, ethanol propanol, butanol, etc.), glycols, oils, water, etc.

Also disclosed is a method of reducing the appearance of fine lines or wrinkles comprising topically applying any one of the compositions disclosed in this specification to skin having fine lines or wrinkles. As noted throughout, the composition can include a plant, plant part, or extract thereof from *Oenothera rosea, Salvia plebeian, Alternanthera philoxeroides, Pyrus pyrifolia, Datura stramonium, Picris hieracioides* ssp. *Japonica, Phoebe neurantha, Acanthopanax gracilistylus, Osmanthus fragrans, Michelia chapensis, Rhododendron spinuliferum, Dendrobenthamia capitata, Ficus microcarpa, Vitex negundo, Sequoia sempervirens, Hypericum forrestii, Ficus pumila, Cercis chinensis, Rhododendron decorum, Ficus retusa* ssp. *nitida, Berchemia polyphylla* var. *leioclada, Elaeocarpus decipiens, Quercus variabilis, Prunus serrulata, Melastoma normale, Lycium chinensis, Chamaecyparis pisifera, Millettia dielsiana, Plumbago auriculata, Nandina domestica, Smilax bockii, Schima wallichii, Carissa spinarum, Wisteria floribunda, Schima argentea, Acacia decurrens* var. *dealbata, Viburnum ichangense, Conyza sumatrensis, Lantana camara, Euonymus bungeanus, Loropetalum chinensis* var. *rubrum, Jasminum mesnyi, Stellaria saxatilis, Elscholtzia cypriani, Daucus carota, Bougainvillea glabra, Serissa serissoides, Antidesma acidum, Sargentodoxa cuneata, Ajuga forrestii, Terminalia chebula, Paederia scandens, Lonicera japonica, Achyranthes bidentata, Hedera nepalensis, Canna chinensis, Ephedra sinica, Dichlrocephala auriculata, Prunus mume* var. *viridicalyx, Castanea molissima, Elaeagnus bockii, Parkia biglobosa, cinnamomum parthenoxylon, Euphorbia esula, Sauropus androgynus, Chamaecrista mimosoides, Crotolaria zanzibarica, Castanopsis eyrei, Girardinia palmate, Phoenix roebelenii, Vinca major, Swertia macrosperma, Onosma paniculatum, Polygonum multiflorum, Gerbera jamesonii, Astragalus membranaceus, Duranta repens, Callicarpa macrophylla, Livistona chinensis, Incarvillea arguta, Lepidium virginicum, Fagopyrum cymosum, Quercus rehderiana, Cunninghamia lanceolata*, and/or *Deutzia glomeruliflora*. The composition can include any one of, any combination of, all of, or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, or 85 of said plants, plant parts, and/or extracts thereof. The plant part can be the whole plant or part of the plant (e.g., root, bark, sap, stem, leaf, flower, seed, leaf, stem, root, flower, seed, sap, bark, etc.). The extract can be from the whole plant or part of the plant (e.g., root, bark, sap, stem, leaf, flower, seed, leaf, stem, root, flower, seed, sap, bark, etc.). The extract can be an aqueous extract or a non-aqueous extract. The extract can be extracted with alcohol (e.g., methanol, ethanol propanol, butanol, etc.), glycols, oils, water, etc.

In certain embodiments, compositions of the present invention can decrease the amount of internal oxidation and/or external oxidative damage in a cell. In other aspects, the compositions can increase collagen synthesis in a cell. The compositions can also reduce skin inflammation, such as by reducing inflammatory cytokine production in a cell. Non-limiting examples of such cells include human epidermal keratinocyte, human fibroblast dermal cell, human melanocytes, three dimensional human cell-derived in vitro tissue equivalents comprising human keratinocytes, human fibroblasts, or human melanocytes, or any combination thereof (e.g., combination of human keratinocytes and human fibroblasts or a combination of human keratinocytes and human melanocytes).

Also disclosed is a method of treating hyperpigmentation comprising applying the compositions of the present invention to the skin. The method can also comprise identifying a person in need of treating hyperpigmentation and applying the composition to a portion of the skin exhibiting hyperpigmentation. Additional methods contemplated by the inventors include methods for reducing the appearance of an age spot, a skin discoloration, or a freckle, reducing or preventing the appearance of fine lines or wrinkles in skin, or increasing the firmness of skin by applying the compositions of the present invention to skin in need of such treatment. As noted throughout, the composition can include a plant, plant part, or extract thereof from *Oenothera rosea, Salvia plebeian, Alternanthera philoxeroides, Pyrus pyrifolia, Datura stramonium, Picris hieracioides* ssp. *Japonica, Phoebe neurantha, Acanthopanax gracilistylus, Osmanthus fragrans, Michelia chapensis, Rhododendron spinuliferum, Dendrobenthamia capitata, Ficus microcarpa, Vitex negundo, Sequoia sempervirens, Hypericum forrestii, Ficus pumila, Cercis chinensis, Rhododendron decorum, Ficus retusa* ssp. *nitida, Berchemia polyphylla* var. *leioclada, Elaeocarpus decipiens, Quercus variabilis, Prunus serrulata, Melastoma normale, Lycium chinensis, Chamaecyparis pisifera, Millettia dielsiana, Plumbago auriculata, Nandina domestica, Smilax bockii, Schima wallichii, Carissa spinarum, Wisteria floribunda, Schima argentea, Acacia decurrens* var. *dealbata, Viburnum ichangense, Conyza sumatrensis, Lantana camara, Euonymus bungeanus, Loropetalum chinensis* var. *rubrum, Jasminum mesnyi, Stellaria saxatilis, Elscholtzia cypriani, Daucus carota, Bougainvillea glabra, Serissa serissoides, Antidesma acidum, Sargentodoxa cuneata, Ajuga forrestii, Terminalia chebula, Paederia scandens, Lonicera japonica, Achyranthes bidentata, Hedera nepalensis, Canna chinensis, Ephedra sinica, Dichlrocephala auriculata, Prunus mume* var. *viridicalyx, Castanea molissima, Elaeagnus bockii, Parkia biglobosa, cinnamomum parthenoxylon, Euphorbia esula, Sauropus androgynus, Chamaecrista mimosoides, Crotolaria zanzibarica, Castanopsis eyrei, Girardinia palmate, Phoenix roebelenii, Vinca major, Swertia macrosperma, Onosma paniculatum, Polygonum multiflorum, Gerbera jamesonii, Astragalus membranaceus, Duranta repens, Callicarpa macrophylla, Livistona chinensis, Incarvillea arguta, Lepidium virginicum, Fagopyrum cymosum, Quercus rehderiana, Cunninghamia lanceolata*, and/or *Deutzia glomeruliflora*. In a particular embodiment, the extract use dis *Ephedra sinica* extract (e.g., such an extract as prepared in accordance with FIG. 1 of the present invention). The composition can include any one of, any combination of, all of, or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, or 85 of said plants, plant parts, and/or extracts thereof. The plant part can be the whole plant or part of the plant (e.g., root, bark, sap, stem, leaf, flower, seed, leaf, stem, root, flower, seed, sap, bark, etc.). The extract can be from the whole plant or part of the plant (e.g., root, bark, sap, stem, leaf, flower, seed, leaf, stem, root, flower, seed, sap, bark, etc.). The extract can be an aqueous extract or a non-aqueous extract. The extract can be extracted with alcohol (e.g., methanol, ethanol propanol, butanol, etc.), glycols, oils, water, etc.

In yet another aspect of the present invention there is disclosed a method of treating or preventing a wide variety of diseases comprising administering to a patient in need of treatment any one of the compositions of the present invention. As noted throughout, the composition can include a plant, plant part, or extract thereof from *Oenothera rosea,*

*Salvia plebeian, Alternanthera philoxeroides, Pyrus pyrifolia, Datura stramonium, Picris hieracioides* ssp. *Japonica, Phoebe neurantha, Acanthopanax gracilistylus, Osmanthus fragrans, Michelia chapensis, Rhododendron spinuliferum, Dendrobenthamia capitata, Ficus microcarpa, Vitex negundo, Sequoia sempervirens, Hypericum forrestii, Ficus pumila, Cercis chinensis, Rhododendron decorum, Ficus retusa* ssp. *nitida, Berchemia polyphylla* var. *leioclada, Elaeocarpus decipiens, Quercus variabilis, Prunus serrulata, Melastoma normale, Lycium chinensis, Chamaecyparis pisifera, Millettia dielsiana, Plumbago auriculata, Nandina domestica, Smilax bockii, Schima wallichii, Carissa spinarum, Wisteria floribunda, Schima argentea, Acacia decurrens* var. *dealbata, Viburnum ichangense, Conyza sumatrensis, Lantana camara, Euonymus bungeanus, Loropetalum chinensis* var. *rubrum, Jasminum mesnyi, Stellaria saxatilis, Elscholtzia cypriani, Daucus carota, Bougainvillea glabra, Serissa serissoides, Antidesma acidum, Sargentodoxa cuneata, Ajuga forrestii, Terminalia chebula, Paederia scandens, Lonicera japonica, Achyranthes bidentata, Hedera nepalensis, Canna chinensis, Ephedra sinica, Dichlrocephala auriculata, Prunus mume* var. *viridicalyx, Castanea molissima, Elaeagnus bockii, Parkia biglobosa, cinnamomum parthenoxylon, Euphorbia esula, Sauropus androgynus, Chamaecrista mimosoides, Crotolaria zanzibarica, Castanopsis eyrei, Girardinia palmate, Phoenix roebelenii, Vinca major, Swertia macrosperma, Onosma paniculatum, Polygonum multiforum, Gerbera jamesonii, Astragalus membranaceus, Duranta repens, Callicarpa macrophylla, Livistona chinensis, Incarvillea arguta, Lepidium virginicum, Fagopyrum cymosum, Quercus rehderiana, Cunninghamia lanceolata,* and/or *Deutzia glomeruliflora.* The composition can include any one of, any combination of, all of, or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, or 85 of said plants, plant parts, and/or extracts thereof. The plant part can be the whole plant or part of the plant (e.g., root, bark, sap, stem, leaf, flower, seed, leaf, stem, root, flower, seed, sap, bark, etc.). The extract can be from the whole plant or part of the plant (e.g., root, bark, sap, stem, leaf, flower, seed, leaf, stem, root, flower, seed, sap, bark, etc.). The extract can be an aqueous extract or a non-aqueous extract. The extract can be extracted with alcohol (e.g., methanol, ethanol propanol, butanol, etc.), glycols, oils, water, etc. The composition can be formulated as a topical composition, an ingestible composition, an injectable composition, an aerosolized composition, etc. Non-limiting examples of diseases that can be treated or prevented with such compositions include AIDS, autoimmune diseases (e.g., rheumatoid arthritis, multiple sclerosis, diabetes-insulin-dependent and non-independent, systemic lupus erythematosus and Graves disease), cancer (e.g., malignant, benign, metastatic, precancer), cardiovascular diseases (e.g., heart disease or coronary artery disease, stroke-ischemic and hemorrhagic, and rheumatic heart disease), diseases of the nervous system, and infection by pathogenic microorganisms (e.g., Athlete's Foot, Chickenpox, Common cold, Diarrheal diseases, Flu, Genital herpes, Malaria, Meningitis, Pneumonia, Sinusitis, Skin diseases, Strep throat, Tuberculosis, Urinary tract infections, Vaginal infections, Viral hepatitis), inflammation (e.g., allergy, asthma), prion diseases (e.g., CID, kuru, GSS, FFI), obesity, etc.

Also disclosed is a method thickening hair or treating or preventing hair loss on the scalp (e.g., male-pattern baldness, female-pattern baldness, cicatricial alopecia, alopecia areata telogen effluvium, traction alopecia, anagen effluvium), eyebrows, or eyelashes comprising administering to a patient in need of any such treatment any one of the compositions of the present invention. As noted throughout, the composition can include a plant, plant part, or extract thereof from *Oenothera rosea, Salvia plebeian, Alternanthera philoxeroides, Pyrus pyrifolia, Datura stramonium, Picris hieracioides* ssp. *Japonica, Phoebe neurantha, Acanthopanax gracilistylus, Osmanthus fragrans, Michelia chapensis, Rhododendron spinuliferum, Dendrobenthamia capitata, Ficus microcarpa, Vitex negundo, Sequoia sempervirens, Hypericum forrestii, Ficus pumila, Cercis chinensis, Rhododendron decorum, Ficus retusa* ssp. *nitida, Berchemia polyphylla* var. *leioclada, Elaeocarpus decipiens, Quercus variabilis, Prunus serrulata, Melastoma normale, Lycium chinensis, Chamaecyparis pisifera, Millettia dielsiana, Plumbago auriculata, Nandina domestica, Smilax bockii, Schima wallichii, Carissa spinarum, Wisteria floribunda, Schima argentea, Acacia decurrens* var. *dealbata, Viburnum ichangense, Conyza sumatrensis, Lantana camara, Euonymus bungeanus, Loropetalum chinensis* var. *rubrum, Jasminum mesnyi, Stellaria saxatilis, Elscholtzia cypriani, Daucus carota, Bougainvillea glabra, Serissa serissoides, Antidesma acidum, Sargentodoxa cuneata, Ajuga forrestii, Terminalia chebula, Paederia scandens, Lonicera japonica, Achyranthes bidentata, Hedera nepalensis, Canna chinensis, Ephedra sinica, Dichlrocephala auriculata, Prunus mume* var. *viridicalyx, Castanea molissima, Elaeagnus bockii, Parkia biglobosa, cinnamomum parthenoxylon, Euphorbia esula, Sauropus androgynus, Chamaecrista mimosoides, Crotolaria zanzibarica, Castanopsis eyrei, Girardinia palmate, Phoenix roebelenii, Vinca major, Swertia macrosperma, Onosma paniculatum, Polygonum multiflorum, Gerbera jamesonii, Astragalus membranaceus, Duranta repens, Callicarpa macrophylla, Livistona chinensis, Incarvillea arguta, Lepidium virginicum, Fagopyrum cymosum, Quercus rehderiana, Cunninghamia lanceolata,* and/or *Deutzia glomeruliflora.* The composition can include any one of, any combination of, all of, or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, or 85 of said plants, plant parts, and/or extracts thereof. The plant part can be the whole plant or part of the plant (e.g., root, bark, sap, stem, leaf, flower, seed, leaf, stem, root, flower, seed, sap, bark, etc.). The extract can be from the whole plant or part of the plant (e.g., root, bark, sap, stem, leaf, flower, seed, leaf, stem, root, flower, seed, sap, bark, etc.). The extract can be an aqueous extract or a non-aqueous extract. The extract can be extracted with alcohol (e.g., methanol, ethanol propanol, butanol, etc.), glycols, oils, water, etc. The composition can be formulated as a topical composition, an ingestible composition, an injectable composition, an aerosolized composition, a foam based composition etc. An assay that can be used to test a composition's ability to thicken hair or treat or prevent hair loss is to apply test composition to a targeted area and measure new hair growth or rate of hair loss when compared with a controlled area that is not receiving the test composition. The method can also include combining any one of the compositions of the present invention with known hair loss or hair thickening treatments (e.g., 5-α reductase inhibitors (e.g., finasteride, dutasteride, saw palmetto extract etc.), vasodilators (e.g., minoxidil), ketoconazole, hair transplantation procedures, hair multiplication procedures, laser therapy, caffeine, etc.).

In one particular non-limiting embodiment, the extract or extracts used in any one of the treatment methods described above and throughout this specification and claims is prepared in accordance with the procedures described in FIG. 1. The contents of FIG. 1 are incorporated by reference.

Multipurpose compositions are also contemplated. For instance, compositions that can have antioxidant properties, inhibit or reduce melanin production, inhibit or reduce tyrosinase activity, inhibit or reduce TNF-α activity, or increase or stimulate collagen production, or any 2, 3, 4, or all of such properties is contemplated. Such compositions can be prepared in view of the information provided in the Detailed Description and Examples sections of this specification, which explains the abilities of the extracts.

The compositions of the present invention can also take the form of topically spreadable compositions, sprayable compositions, aerosolized compositions, injectable compositions, edible compositions, compositions in tablet, gel cap, or pill form. The extract used within the compositions and methods of the present invention can be aqueous extracts, alcoholic extracts, glycolic extracts, oil extracts, or any combination thereof. The compositions can be in powdered form, liquid form, or aerosolized form. The extracts can prepared in accordance with the process described in FIG. 1.

It is also contemplated that the compositions disclosed throughout this specification can be used with leave-on or rinse-off products. By way of example, a leave-on product can be one that is topically applied to skin and remains on the skin for a period of time (e.g., at least 5, 6, 7, 8, 9, 10, 20, or 30 minutes, or at least 1, 2, 3, 4, 5, 6, 7, 8, 9, 10, 11, 12, 13, 14, 15, 16, 17, 18, 19, 20, 21, 22, 23 or 24 hours, or over night or throughout the day). Alternatively, a rinse-off product can be a product that is intended to be applied to the skin and then removed or rinsed from the skin (e.g., with water) within a period of time such as less than 5, 4, 3, 2, or 1 minute. An example of a rinse of product can be a skin cleanser, shampoo, conditioner, or soap. An example of a leave-on product can be a skin moisturizer, sunscreen, mask, overnight cream, or a day cream.

Kits that include the compositions of the present invention are also contemplated. In certain embodiments, the composition is comprised in a container. The container can be a bottle, dispenser, or package. The container can dispense a pre-determined amount of the composition. In certain aspects, the compositions is dispensed in a spray, dollop, or liquid. The container can include indicia on its surface. The indicia can be a word, an abbreviation, a picture, or a symbol.

Also contemplated is a product comprising a composition of the present invention. In non-limiting aspects, the product can be a cosmetic product. The cosmetic product can be those described in other sections of this specification or those known to a person of skill in the art. Non-limiting examples of products include a moisturizer, a cream, a lotion, a skin softener, a foundation, a night cream, a lipstick, a cleanser, a toner, a sunscreen, a mask, an anti-aging product, a deodorant, an antiperspirant, a perfume, a cologne, etc.

It is also contemplated that compositions of the present invention can be included into food-based products (e.g., beverages, fortified water, energy drinks, nutritional drinks, solid foods, vitamins, supplements, etc.) and pharmaceutical products (e.g., pills, tablets, gel capsules, injectable solutions, drugs, etc.). "Supplements" can include vitamins, minerals, herbs or other botanicals, amino acids, enzymes and metabolites. Such supplements are suitable for oral consumption and can be administered orally.

Further, the contents of U.S. application Ser. No. 12/869, 352, filed Aug. 26, 2010, International Application No. PCT/US10/46791, filed Aug. 26, 2010, and U.S. Provisional Application No. 61/237,087, filed Aug. 26, 2009, are incorporated by reference into the present application. The contents of these referenced applications can be used in combination with the contents in the present specification.

It is contemplated that any embodiment discussed in this specification can be implemented with respect to any method or composition of the invention, and vice versa. Furthermore, compositions of the invention can be used to achieve methods of the invention.

In one embodiment, the topical skin compositions of the current invention are pharmaceutically elegant. "Pharmaceutically elegant" describes a composition that has particular tactile properties which feel pleasant on the skin (e.g., compositions that are not too watery or greasy, compositions that have a silky texture, compositions that are non-tacky or sticky, etc.). Pharmaceutically elegant can also relate to the creaminess or lubricity properties of the composition or to the moisture retaining properties of the composition.

"Keratinous tissue" includes keratin-containing layers disposed as the outermost protective covering of mammals and includes, but is not limited to, skin, hair and nails.

"Topical application" means to apply or spread a composition onto the surface of keratinous tissue. "Topical skin composition" includes compositions suitable for topical application on keratinous tissue. Such compositions are typically dermatologically-acceptable in that they do not have undue toxicity, incompatibility, instability, allergic response, and the like, when applied to skin. Topical skin care compositions of the present invention can have a selected viscosity to avoid significant dripping or pooling after application to skin.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The terms "inhibiting" or "reducing" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented below.

FIG. 1. Extraction process used to obtain extracts from each of the following plants (note that although the whole plant was used in the extract process for each of the Extracts to obtain the data in the Examples, plant parts are also contemplated and can be used by the process described in FIG. 1—e.g., stem, bark, root, flower, seed, fruit, leaf, sap etc.): *Oenothera rosea, Salvia plebeian, Alternanthera philoxeroides, Pyrus pyrifolia, Datura stramonium, Picris hieracioides ssp. Japonica, Phoebe neurantha, Acanthopanax gracilistylus, Osmanthus fragrans, Michelia chapensis, Rhododendron spinuliferum, Dendrobenthamia capitata, Ficus microcarpa, Vitex negundo, Sequoia sempervirens, Hypericum forrestii, Ficus pumila, Cercis chinensis, Rhododendron decorum, Ficus retusa ssp. nitida, Berchemia polyphylla var. leioclada, Elaeocarpus decipiens, Quercus variabilis, Prunus serrulata, Melastoma normale, Lycium chinensis, Chamaecyparis pisifera, Millettia dielsiana, Plumbago auriculata, Nandina domestica, Smilax bockii, Schima wallichii, Carissa spinarum, Wisteria floribunda, Schima argentea, Acacia decurrens var. dealbata, Viburnum ichangense, Conyza sumatrensis, Lantana camara, Euonymus bungeanus, Loropetalum chinensis var. rubrum, Jasminum mesnyi, Stellaria saxatilis, Elscholtzia cypriani, Daucus carota, Bougainvillea glabra, Serissa serissoides, Antidesma acidum, Sargentodoxa cuneata, Ajuga forrestii, Terminalia chebula, Paederia scandens, Lonicera japonica, Achyranthes bidentata, Hedera nepalensis, Canna chinensis, Ephedra sinica, Dichlrocephala auriculata, Prunus mume var. viridicalyx, Castanea molissima, Elaeagnus bockii, Parkia biglobosa, cinnamomum parthenoxylon, Euphorbia esula, Sauropus androgynus, Chamaecrista mimosoides, Crotolaria zanzibarica, Castanopsis eyrei, Girardinia palmate, Phoenix roebelenii, Vinca major, Swertia macrosperma, Onosma paniculatum, Polygonum multiforum, Gerbera jamesonii, Astragalus membranaceus, Duranta repens, Callicarpa macrophylla, Livistona chinensis, Incarvillea arguta, Lepidium virginicum, Fagopyrum cymosum, Quercus rehderiana, Cunninghamia lanceolata,* and *Deutzia glomeruliflora.*

DESCRIPTION OF ILLUSTRATIVE EMBODIMENTS

In today's image conscious society, people are continually looking for a product that can improve the visual appearance of their skin. Often times, aged skin, uneven skin tone, or skin damaged by environmental factors such as UV light, chronic sun exposure, environmental pollutants, chemicals, disease pathologies, or smoking, is associated with unattractive skin. Previous attempts to improve the visual appearance of skin has been shown to have various drawbacks such as skin irritation and prolonged recovery periods.

The present invention is an effective alternative to the use of compositions and ingredients currently used to treat aged skin, environmentally-damaged skin, uneven skin tone, and other skin conditions. In one non-limiting embodiment, the compositions of the present invention can be used to treat irritation of the skin and to improve the skin's visual appearance, physiological functions, clinical properties, or biophysical properties by providing a composition of the present invention to an area of the skin that needs such treatment. As noted throughout this specification, the compositions can include a plant, plant part, or extract thereof from *Oenothera rosea, Salvia plebeian, Alternanthera philoxeroides, Pyrus pyrifolia, Datura stramonium, Picris hieracioides ssp. Japonica, Phoebe neurantha, Acanthopanax gracilistylus, Osmanthus fragrans, Michelia chapensis, Rhododendron spinuliferum, Dendrobenthamia capitata, Ficus microcarpa, Vitex negundo, Sequoia sempervirens, Hypericum forrestii, Ficus pumila, Cercis chinensis, Rhododendron decorum, Ficus retusa ssp. nitida, Berchemia polyphylla var. leioclada, Elaeocarpus decipiens, Quercus variabilis, Prunus serrulata, Melastoma normale, Lycium chinensis, Chamaecyparis pisifera, Millettia dielsiana, Plumbago auriculata, Nandina domestica, Smilax bockii, Schima wallichii, Carissa spinarum, Wisteria floribunda, Schima argentea, Acacia decurrens var. dealbata, Viburnum ichangense, Conyza sumatrensis, Lantana camara, Euonymus bungeanus, Loropetalum chinensis var. rubrum, Jasminum mesnyi, Stellaria saxatilis, Elscholtzia cypriani, Daucus carota, Bougainvillea glabra, Serissa serissoides, Antidesma acidum, Sargentodoxa cuneata, Ajuga forrestii, Terminalia chebula, Paederia scandens, Lonicera japonica, Achyranthes bidentata, Hedera nepalensis, Canna chinensis, Ephedra sinica, Dichlrocephala auriculata, Prunus mume var. viridicalyx, Castanea molissima, Elaeagnus bockii, Parkia biglobosa, cinnamomum parthenoxylon, Euphorbia esula, Sauropus androgynus, Chamaecrista mimosoides, Crotolaria zanzibarica, Castanopsis eyrei, Girardinia palmate, Phoenix roebelenii, Vinca major, Swertia macrosperma, Onosma paniculatum, Polygonum multiflorum, Gerbera jamesonii, Astragalus membranaceus, Duranta repens, Callicarpa macrophylla, Livistona chinensis, Incarvillea arguta, Lepidium virginicum, Fagopyrum cymosum, Quercus rehderiana, Cunninghamia lanceolata,* and/or *Deutzia glomeruliflora.* In particular aspects, the compositions of the present invention can include any one of, any combination of, all of, or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, or 85 of said plants, plant parts, and/or extracts thereof.

These and other non-limiting aspects of the present invention are described in further detail below.

A. Plants and Extracts Thereof

The plants and extracts thereof of can be obtained by standard cultivation and extraction techniques known to those having ordinary skill in the art. Non-limiting examples of such techniques are provided below, in the Examples, and in FIG. 1. In addition, these extracts can be obtained through third parties such as Kunming Institute of Botany, Chinese Academy of Sciences, Yunnan, CHINA ("KM") (e.g., the plant material used in the Examples was obtained from KM.

For instance, a person of ordinary skill in the art would be able to isolate any one of the extracts identified below from parts of the corresponding plant by using any suitable method known in the art. In one non-limiting example, the plant (or any part of the plant such as the leaves, stems, bark, roots, fruit, flowers or flower buds, seeds, seed pods, sap, whole plant, etc.) can be disrupted by mechanical means which results in a puree. The puree is then processed to be substantially free of impurities or undesired solids. The puree can then be poured into a shallow vessel and quickly exposed to low temperature, i.e., flash frozen, for example at −20° C. or lower, preferably under a vacuum for removal of water content (lyophilization). The resultant extract can then be used in the compositions of the present invention.

In other aspects, aqueous, alcoholic, or oil based extraction techniques, or combinations thereof, can be used on the whole plant or any part thereof of (e.g., leaves, stems, bark, roots, fruit, flowers or flower buds, seeds, seed pods, sap, whole plant, etc.) to produce an extract. In such a process, the desired part of the plant or the whole plant is crushed up (e.g., blender) and then subjected to a desired solvent (e.g., water, alcohol, water/alcohol, or oil based solvents) to obtain the desired extract. The extract can then be stored in liquid form, lyophilized, or subject to further processing techniques (e.g., heating, cooling, etc.). Extraction processes are well-known to those having ordinary skill in the extract field (e.g., maceration, infusion, percolation, digestion, decoction, hot continuous extraction, aqueous-alcoholic extract, counter current extract, microwave assisted extraction, ultrasound extraction, supercritical fluid extracts, phytonic extract (e.g., with hydro-flouro-carbon solvents), etc.

General information about the plants are provided below.

1. *Oenothera rosea*

*Oenothera rosea*, also known as pink evening primrose or rose of mexico, is a perennial flowering plant that can reach 40 centimeters in height. It has green leaves and a long stems that lead to a flower. It is capable of producing flowers and seeds. This plant is native to Mexico and Texas, USA.

The inventors have discovered that extracts of *Oenothera rosea* have several biological activities, which can be beneficial to skin. Non-limiting examples of some of these biological activities include antioxidant properties and the ability to inhibit TNF-α activity. All of the different portions of *Oenothera rosea* can be used to obtain the corresponding extract. Non-limiting examples include its leaves, stems, bark, roots, fruit, flowers or flower buds, seeds, sap, and the entire plant.

2. *Salvia* plebeian

*Salvia* plebeian, can be obtained from gum tree branches that are native to India.

The inventors have discovered that extracts of *Salvia* plebeian have several biological activities, which can be beneficial to skin. Non-limiting examples of some of these biological activities include antioxidant properties and the ability to inhibit TNF-α activity.

3. *Alternanthera philoxeroides*

*Alternanthera philoxeroides* typically grows around, in or under water and is therefore known as an emrsed plant. Its stems are pinkish and can become hollow when larger, to 1 m (3.3 ft) long. Its leaves are narrowly elliptic or spatulate, to 9 cm (3.5 in) long. It can product flowers that are bisexual in round white heads on long stalks from upper leaf axils; each flower with 4-5 thin, papery bracts, 5 stamens, 1 pistil. It also products fruit. This plant can be found throughout the world (e.g., China, India, and U.S.).

The inventors have discovered that extracts of *Alternanthera philoxeroides* have several biological activities, which can be beneficial to skin. Non-limiting examples of some of these biological activities include the ability to inhibit both TNF-α and tyrosinase activity. All of the different portions of *Alternanthera philoxeroides* can be used to obtain the corresponding extract. Non-limiting examples include its leaves, stems, bark, roots, fruit, flowers or flower buds, seeds, sap, and the entire plant.

4. *Pyrus pyrifolia*

*Pyrus pyrifolia* is a pear tree species that is native to China, Japan, and Korea. It has green leaves, white flowers, and can produce fruit and seeds.

The inventors have discovered that extracts of *Pyrus pyrifolia* have several biological activities, which can be beneficial to skin. Non-limiting examples of one of these activities is its ability to act as an antioxidant. All of the different portions of *Pyrus pyrifolia* can be used to obtain the corresponding extract. Non-limiting examples include its leaves, stems, bark, roots, fruit, flowers or flower buds, seeds, sap, and the entire plant.

5. *Picris hieracioides* ssp. *japonica*

*Picris hieracioides* ssp. *japonica*, also known as kozorina, is a small plant that has green leaves and can reach 1-3 feet in height. It is capable of producing flowers, fruit, and seeds. This plant is native to Russia, Kazakhstan, Mongolia, China, and Japan.

The inventors have discovered that extracts of *Picris hieracioides* ssp. *Japonica* have several biological activities, which can be beneficial to skin. Non-limiting examples of some of these biological activities include antioxidant properties, the ability to stimulate collegen synthesis, and the ability to inhibit both TNF-α and tyrosinase activity. All of the different portions of *Picris hieracioides* ssp. *japonica* can be used to obtain the corresponding extract. Non-limiting examples include its leaves, stems, bark, roots, fruit, flowers or flower buds, seeds, sap, and the entire plant.

6. *Phoebe neurantha*

*Phoebe neurantha* is a large shrub that has gray/black bark and is capable of producing leaves and flowers. It is native to China.

The inventors have discovered that extracts of *Phoebe neurantha* have several biological activities, which can be beneficial to skin. Non-limiting examples of some of these biological activities include antioxidant properties and the ability to inhibit both TNF-α and tyrosinase activity. All of the different portions of *Phoebe neurantha* can be used to obtain the corresponding extract. Non-limiting examples include its leaves, stems, bark, roots, fruit, flowers or flower buds, seeds, sap, and the entire plant.

7. *Acanthopanax gracilistylus*

*Acanthopanax gracilistylus* is a deciduous shrub with upright to slightly arching stems, small, fresh green, trilobed to palmately divided leaves and several axillary as well as terminal round clusters of decorative, bluish black berries in late summer and autumn. It is native to China.

The inventors have discovered that extracts of *Acanthopanax gracilistylus* have several biological activities, which can be beneficial to skin. Non-limiting examples of some of these biological activities include antioxidant properties. All of the different portions of *Acanthopanax gracilistylus* can be used to obtain the corresponding extract. Non-limiting examples include its leaves, stems, bark, roots, fruit, flowers or flower buds, seeds, sap, and the entire plant.

8. *Acanthopanax gracilistylus*

*Acanthopanax gracihstylus* is a deciduous shrub with upright to slightly arching stems, small, fresh green, trilobed to palmately divided leaves and several axillary as well as terminal round clusters of decorative, bluish black berries in late summer and autumn. It is native to China.

The inventors have discovered that extracts of *Acanthopanax gracilistylus* have several biological activities, which can be beneficial to skin. Non-limiting examples of some of these biological activities include antioxidant properties. All of the different portions of *Acanthopanax gracilistylus* can be used to obtain the corresponding extract. Non-limiting examples include its leaves, stems, bark, roots, fruit, flowers or flower buds, seeds, sap, and the entire plant.

9. *Osmanthus fragrans*

*Osmanthus fragrans* is an evergreen shrub that has leaves and can product flowers and seeds. It is native to Asia (e.g., China, Taiwan, and Japan).

The inventors have discovered that extracts of *Osmanthus fragrans* have several biological activities, which can be beneficial to skin. Non-limiting examples of some of these biological activities include antioxidant properties, the ability to increase collagen stimulation/production in skin, and the ability to inhibit TNF-α and tyrosinase activity. All of the different portions of *Osmanthus fragrans* can be used to obtain the corresponding extract. Non-limiting examples include its leaves, stems, bark, roots, fruit, flowers or flower buds, seeds, sap, and the entire plant.

10. *Michelia chapensis*

*Michelia chapensis* is a large tree that has leaves and can product white flowers. It is native to China.

The inventors have discovered that extracts of *Michelia chapensis* have several biological activities, which can be beneficial to skin. Non-limiting examples of some of these biological activities include antioxidant properties and the ability to inhibit TNF-α and tyrosinase activity. All of the different portions of *Michelia chapensis* can be used to obtain the corresponding extract. Non-limiting examples include its leaves, stems, bark, roots, fruit, flowers or flower buds, seeds, sap, and the entire plant.

11. *Rhododendron spinuliferum*

*Rhododendron spinuliferum* is a shrub that has brownish red branches that has leaves and can produce flowers. It is native to China.

The inventors have discovered that extracts of *Rhododendron spinuliferum* have several biological activities, which can be beneficial to skin. Non-limiting examples of some of these biological activities include antioxidant properties and the ability to inhibit TNF-α and tyrosinase activity. All of the different portions of *Rhododendron spinuliferum* can be used to obtain the corresponding extract. Non-limiting examples include its leaves, stems, bark, roots, fruit, flowers or flower buds, seeds, sap, and the entire plant.

12. *Dendrobenthamia capitata*

*Dendrobenthamia capitata* is a species of a dogwood tree. It produces green leaves, flowers, and seepds. It is native to China, India, Australia, and New Zealand.

The inventors have discovered that extracts of *Dendrobenthamia capitata* have several biological activities, which can be beneficial to skin. Non-limiting examples of some of these biological activities include antioxidant properties and the ability to inhibit TNF-α and tyrosinase activity. All of the different portions of *Dendrobenthamia capitata* can be used to obtain the corresponding extract. Non-limiting examples include its leaves, stems, bark, roots, fruit, flowers or flower buds, seeds, sap, and the entire plant.

13. *Ficus microcarpa*

*Ficus microcarpa* is a banyan that has green leaves and is capable of produces flowers, seeds, and fruit. It is native to Sri Lanka, India, China, and Australia.

The inventors have discovered that extracts of *Ficus microcarpa* have several biological activities, which can be beneficial to skin. Non-limiting examples of some of these biological activities include antioxidant properties and the ability to inhibit TNF-α and tyrosinase activity. All of the different portions of *Ficus microcarpa* can be used to obtain the corresponding extract. Non-limiting examples include its leaves, stems, bark, roots, fruit, flowers or flower buds, seeds, sap, and the entire plant.

14. *Vitex negundo*

*Vitex negundo* is a chaste tree that has green leaves and is capable of producing flowers. It is native to Mediterranean countries and Central Asia.

The inventors have discovered that extracts of *Vitex negundo* have several biological activities, which can be beneficial to skin. Non-limiting examples of some of these biological activities include antioxidant properties. Non-limiting examples include its leaves, stems, bark, roots, fruit, flowers or flower buds, seeds, sap, and the entire plant.

15. *Sequoia sempervirens*

*Sequoia sempervirens* is a large tree that produces green leaves and can product flowers. It is native to the U.S.A. (e.g., Hawaii).

The inventors have discovered that extracts of *Sequoia sempervirens* have several biological activities, which can be beneficial to skin. Non-limiting examples of some of these biological activities include antioxidant properties and the ability to inhibit TNF-α and tyrosinase activity. Non-limiting examples include its leaves, stems, bark, roots, fruit, flowers or flower buds, seeds, sap, and the entire plant.

16. *Hypericum forrestii*

*Hypericum forrestii* is a large tree that produces green leaves and can product flowers. It is native to the U.S.A. (e.g., Hawaii).

The inventors have discovered that extracts of *Hypericum forrestii* have several biological activities, which can be beneficial to skin. Non-limiting examples of some of these biological activities include antioxidant properties and the ability to inhibit tyrosinase activity. Non-limiting examples include its leaves, stems, bark, roots, fruit, flowers or flower buds, seeds, sap, and the entire plant.

17. *Ficus pumila*

*Ficus pumila* is a woody vine that can produce figs. It is native to East Asia.

The inventors have discovered that extracts of *Ficus pumila* have several biological activities, which can be beneficial to skin. Non-limiting examples of some of these biological activities include antioxidant properties and the ability to inhibit tyrosinase activity. Non-limiting examples include its leaves, stems, bark, roots, fruit, flowers or flower buds, seeds, sap, and the entire plant.

18. *Cercis chinensis*

*Cercis chinensis* is a desiduous tree that has green leaves and is capable of producing reddish flowers and seeds. It is native to China.

The inventors have discovered that extracts of *Cercis chinensis* have several biological activities, which can be beneficial to skin. Non-limiting examples of some of these biological activities include antioxidant properties. Non-limiting examples include its leaves, stems, bark, roots, fruit, flowers or flower buds, seeds, sap, and the entire plant.

19. *Rhododendron decorum*

*Rhododendron decorum* is a shrub that can produce green leaves, flowers, and seeds. It is native to China.

The inventors have discovered that extracts of *Rhododendron decorum* have several biological activities, which can be beneficial to skin. Non-limiting examples of some of these biological activities include antioxidant properties and the ability to inhibit TNF-α activity. Non-limiting examples include its leaves, stems, bark, roots, fruit, flowers or flower buds, seeds, sap, and the entire plant.

20. *Ficus retusa* ssp. *nitida*

*Ficus retusa* ssp. *nitida* is an evergreen tree that is native to Malaysia and Borneo.

The inventors have discovered that extracts of *Ficus retusa* ssp. *nitida* have several biological activities, which can be beneficial to skin. Non-limiting examples of some of these biological activities include antioxidant properties and the ability to inhibit TNF-α activity. Non-limiting examples include its leaves, stems, bark, roots, fruit, flowers or flower buds, seeds, sap, and the entire plant.

21. *Berchemia polyphylla* var. *leioclada*

*Berchemia polyphylla* var. *leioclada* is a plant that has green leaves and is capable of producing flowers, fruits, and seeds. It is native to China.

The inventors have discovered that extracts of *Berchemia polyphylla* var. *leioclada* have several biological activities, which can be beneficial to skin. Non-limiting examples of some of these biological activities include antioxidant properties and the ability to inhibit tyrosinase activity. Non-limiting examples include its leaves, stems, bark, roots, fruit, flowers or flower buds, seeds, sap, and the entire plant.

22. *Elaeocarpus decipiens*

*Elaeocarpus decipiens* is a tree that has green leaves and is capable of producing flowers, blue berries, and seeds. It is native to China and Japan.

The inventors have discovered that extracts of *Elaeocarpus decipiens* have several biological activities, which can be beneficial to skin. Non-limiting examples of some of these biological activities include antioxidant properties and the ability to inhibit TNF-α and tyrosinase activity. Non-limiting examples include its leaves, stems, bark, roots, fruit, flowers or flower buds, seeds, sap, and the entire plant.

23. *Quercus variabilis*

*Quercus variabilis* is a species of oak and is native to China, Japan, and Korea.

The inventors have discovered that extracts of *Quercus variabilis* have several biological activities, which can be beneficial to skin. Non-limiting examples of some of these biological activities include antioxidant properties and the ability to inhibit TNF-α and tyrosinase activity. Non-limiting examples include its leaves, stems, bark, roots, fruit, flowers or flower buds, seeds, sap, and the entire plant.

24. *Prunus serrulata*

*Prunus serrulata* is a species of cherry that is capable of producing flowers and cherries. It is native to China, Japan, and Korea.

The inventors have discovered that extracts of *Prunus serrulata* have several biological activities, which can be beneficial to skin. Non-limiting examples of some of these biological activities include antioxidant properties and the ability to inhibit TNF-α activity. Non-limiting examples include its leaves, stems, bark, roots, fruit, flowers or flower buds, seeds, sap, and the entire plant.

25. *Melastoma normale*

*Melastoma normale* is a plant that has green leaves and is native to China.

The inventors have discovered that extracts of *Melastoma normale* have several biological activities, which can be beneficial to skin. Non-limiting examples of some of these biological activities include antioxidant properties and the ability to inhibit TNF-α and tyrosinase activity. Non-limiting examples include its leaves, stems, bark, roots, fruit, flowers or flower buds, seeds, sap, and the entire plant.

26. *Lycium chinensis*

*Lycium chinensis* is a species of the boxthorn family and is a plant that has green leaves and red fruit. It is native to China.

The inventors have discovered that extracts of *Lycium chinensis* have several biological activities, which can be beneficial to skin. Non-limiting examples of some of these biological activities include antioxidant properties, the ability to increase/promote collagen production, and the ability to inhibit tyrosinase activity. Non-limiting examples include its leaves, stems, bark, roots, fruit, flowers or flower buds, seeds, sap, and the entire plant.

27. *Chamaecyparis pisifera*

*Chamaecyparis pisifera* is an evergreen shrub that can produce flowers and fruits. It is native to China and Japan The inventors have discovered that extracts of *Chamaecyparis pisifera* have several biological activities, which can be beneficial to skin. Non-limiting examples of some of these biological activities include antioxidant properties and the ability to inhibit TNF-α and tyrosinase activity. Non-limiting examples include its leaves, stems, bark, roots, fruit, flowers or flower buds, seeds, sap, and the entire plant.

28. *Millettia dielsiana*

*Millettia dielsiana* is a deciduous shrub that can produce flowers. It is native to China.

The inventors have discovered that extracts of *Millettia dielsiana* have several biological activities, which can be beneficial to skin. Non-limiting examples of some of these biological activities include antioxidant properties, the ability to increase/promote collagen production, and the ability to inhibit TNF-α and tyrosinase activity. Non-limiting examples include its leaves, stems, bark, roots, fruit, flowers or flower buds, seeds, sap, and the entire plant.

29. *Plumbago auriculata*

*Plumbago auriculata* is a plant that has green leaves and is capable of producing flowers and fruit. It is native to South Africa.

The inventors have discovered that extracts of *Plumbago auriculata* have several biological activities, which can be beneficial to skin. Non-limiting examples of some of these biological activities include antioxidant properties and the ability to inhibit TNF-α and tyrosinase activity. Non-limiting examples include its leaves, stems, bark, roots, fruit, flowers or flower buds, seeds, sap, and the entire plant.

30. *Nandina domestica*

*Nandina domestica* is a suckering shrub that is native to China and Japan.

The inventors have discovered that extracts of *Nandina domestica* have several biological activities, which can be beneficial to skin. Non-limiting examples of some of these biological activities include antioxidant properties and the ability to inhibit TNF-α and tyrosinase activity. Non-limiting examples include its leaves, stems, bark, roots, fruit, flowers or flower buds, seeds, sap, and the entire plant.

31. *Smilax bockii*

*Smilax bockii* is a plant that has green leaves and is native to China.

The inventors have discovered that extracts of *Smilax bockii* have several biological activities, which can be beneficial to skin. Non-limiting examples of some of these biological activities include the ability to increase/promote collagen production, antioxidant properties, and the ability to inhibit TNF-α activity. Non-limiting examples include its leaves, stems, bark, roots, fruit, flowers or flower buds, seeds, sap, and the entire plant.

32. *Schima wallichii*

*Schima wallichii* is an evergreen tree that can produce flowers. It is native to China and Nepal.

The inventors have discovered that extracts of *Schima wallichii* have several biological activities, which can be beneficial to skin. Non-limiting examples of some of these biological activities include antioxidant properties and the ability to inhibit TNF-α and tyrosinase activity. Non-limiting examples include its leaves, stems, bark, roots, fruit, flowers or flower buds, seeds, sap, and the entire plant.

33. *Carissa spinarum*

*Carissa spinarum* is a large shrub that produces green leaves and is native to tropical regions around the Indian Ocean (e.g., Australia).

The inventors have discovered that extracts of *Carissa spinarum* have several biological activities, which can be beneficial to skin. Non-limiting examples of some of these biological activities include antioxidant properties and the ability to inhibit TNF-α activity. Non-limiting examples include its leaves, stems, bark, roots, fruit, flowers or flower buds, seeds, sap, and the entire plant.

34. *Wisteria floribunda*

*Wisteria floribunda* is a woody vine that is native to Japan.

The inventors have discovered that extracts of *Wisteria floribunda* have several biological activities, which can be beneficial to skin. Non-limiting examples of some of these biological activities include the ability to increase or promote collagen production. Non-limiting examples include its leaves, stems, bark, roots, fruit, flowers or flower buds, seeds, sap, and the entire plant.

35. *Schima argentea*

*Schima argentea* is a tree that has green leaves and is native to China.

The inventors have discovered that extracts of *Schima argentea* have several biological activities, which can be beneficial to skin. Non-limiting examples of some of these biological activities include the ability to inhibit TNF-α and tyrosinase activity. Non-limiting examples include its leaves, stems, bark, roots, fruit, flowers or flower buds, seeds, sap, and the entire plant.

36. *Acacia decurrens* var. *dealbata*

*Acacia decurrens* var. *dealbata* is a shrub that produces green leaves and yellow flowers. It is native to China.

The inventors have discovered that extracts of *Acacia decurrens* var. *dealbata* have several biological activities, which can be beneficial to skin. Non-limiting examples of some of these biological activities include antioxidant properties and the ability to inhibit TNF-α and tyrosinase activity. Non-limiting examples include its leaves, stems, bark, roots, fruit, flowers or flower buds, seeds, sap, and the entire plant.

37. *Viburnum ichangense*

*Viburnum ichangense* is a plant that can product fragrant white flower clusters. It is native to China.

The inventors have discovered that extracts of *Viburnum ichangense* have several biological activities, which can be beneficial to skin. Non-limiting examples of some of these biological activities include antioxidant properties, the ability to increase or promote collagen production, and the ability to inhibit TNF-α and tyrosinase activity. Non-limiting examples include its leaves, stems, bark, roots, fruit, flowers or flower buds, seeds, sap, and the entire plant.

38. *Conyza sumatrensis*

*Conyza sumatrensis* is a small plant that can product green leaves and white flowers. It is native to North America and sub-tropical South America.

The inventors have discovered that extracts of *Conyza sumatrensis* have several biological activities, which can be beneficial to skin. Non-limiting examples of some of these biological activities include the ability to increase or promote collagen production and the ability to inhibit TNF-α and tyrosinase activity. Non-limiting examples include its leaves, stems, bark, roots, fruit, flowers or flower buds, seeds, sap, and the entire plant.

39. *Lantana camara*

*Lantana camara* is a small flowering plant that can produce purple and yellow flowers. It is native to the American topics (e.g., Mexico and Central America).

The inventors have discovered that extracts of *Lantana camara* have several biological activities, which can be beneficial to skin. Non-limiting examples of some of these biological activities include antioxidant properties and the ability to inhibit TNF-α activity. Non-limiting examples include its leaves, stems, bark, roots, fruit, flowers or flower buds, seeds, sap, and the entire plant.

40. *Euonymus bungeanus*

*Euonymus bungeanus* is a large deciduous shrub that is capable of producing red berries. It is native to China.

The inventors have discovered that extracts of *Euonymus bungeanus* have several biological activities, which can be beneficial to skin. Non-limiting examples of some of these biological activities include antioxidant properties and the ability to inhibit TNF-α and tyrosinase activity. Non-limiting examples include its leaves, stems, bark, roots, fruit, flowers or flower buds, seeds, sap, and the entire plant.

41. *Loropetalum chinensis* var. *rubrum*

*Loropetalum chinensis* var. *rubrum* is a small plant that has green leaves and is capable of producing red/purplish flowers. It is native to China.

The inventors have discovered that extracts of *Loropetalum chinensis* var. *rubrum* have several biological activities, which can be beneficial to skin. Non-limiting examples of some of these biological activities include antioxidant properties and the ability to inhibit TNF-α and tyrosinase activity as well as increase or stimulate production of collagen I. Non-limiting examples include its leaves, stems, bark, roots, fruit, flowers or flower buds, seeds, sap, and the entire plant.

42. *Jasminum mesnyi*

*Jasminum mesnyi* is a tall, slender evergreen shrub that can produce yellow flowers. It is native to China.

The inventors have discovered that extracts of *Jasminum mesnyi* have several biological activities, which can be beneficial to skin. Non-limiting examples of some of these biological activities include the ability to inhibit TNF-α and tyrosinase activity. Non-limiting examples include its leaves, stems, bark, roots, fruit, flowers or flower buds, seeds, sap, and the entire plant.

43. *Stellaria saxatilis*

*Stellaria saxatilis* is a small plant that has green leaves and is capable of producing flowers. It is native to Asia.

The inventors have discovered that extracts of *Stellaria saxatilis* have several biological activities, which can be beneficial to skin. Non-limiting examples of some of these biological activities include the ability to inhibit TNF-α and tyrosinase activity. Non-limiting examples include its leaves, stems, bark, roots, fruit, flowers or flower buds, seeds, sap, and the entire plant.

44. *Elscholtzia cypriani*

*Elscholtzia cypriani* is a plant that has green leaves and is native to Asia.

The inventors have discovered that extracts of *Elscholtzia cypriani* have several biological activities, which can be beneficial to skin. Non-limiting examples of some of these biological activities include antioxidant properties and the ability to inhibit TNF-α activity. Non-limiting examples include its leaves, stems, bark, roots, fruit, flowers or flower buds, seeds, sap, and the entire plant.

45. *Daucus carota*

*Daucus carota* is a flowering plant that can produce white flowers. It is native to Europe, Southwest Asia, North America, and Australia.

The inventors have discovered that extracts of *Daucus carota* have several biological activities, which can be beneficial to skin. Non-limiting examples of some of these biological activities include the ability to inhibit TNF-α and tyrosinase activity. Non-limiting examples include its leaves, stems, bark, roots, fruit, flowers or flower buds, seeds, sap, and the entire plant.

46. *Bougainvillea glabra*

*Bougainvillea glabra* is a flowering plant that can produce a wide range of colorful flowers. It is native to Brazil.

The inventors have discovered that extracts of *Bougainvillea glabra* have several biological activities, which can be beneficial to skin. Non-limiting examples of some of these biological activities include the ability to increase or promote collagen production and the ability to inhibit TNF-α and tyrosinase activity. Non-limiting examples include its leaves, stems, bark, roots, fruit, flowers or flower buds, seeds, sap, and the entire plant.

47. *Serissa serissoides*

*Serissa serissoides* is small tree (Bonsai) that can product white flowers. It is native to Japan.

The inventors have discovered that extracts of *Serissa serissoides* have several biological activities, which can be beneficial to skin. Non-limiting examples of some of these biological activities include the ability to increase or promote collagen production and the ability to inhibit TNF-α activity. Non-limiting examples include its leaves, stems, bark, roots, fruit, flowers or flower buds, seeds, sap, and the entire plant.

48. *Antidesma acidum*

*Antidesma acidum* is shrub that can product flowers. It is native to China.

The inventors have discovered that extracts of *Antidesma acidum* have several biological activities, which can be beneficial to skin. Non-limiting examples of some of these biological activities include antioxidant capabilities and the ability to inhibit TNF-α and tyrosinase activity. Non-limiting examples include its leaves, stems, bark, roots, fruit, flowers or flower buds, seeds, sap, and the entire plant.

49. *Sargentodoxa cuneata*

*Sargentodoxa cuneata* is tree that can product flowers. It is native to China.

The inventors have discovered that extracts of *Sargentodoxa cuneata* have several biological activities, which can be beneficial to skin. Non-limiting examples of some of these biological activities include antioxidant capabilities and the ability to inhibit TNF-α and tyrosinase activity. Non-limiting examples include its leaves, stems, bark, roots, fruit, flowers or flower buds, seeds, sap, and the entire plant.

50. *Ajuga forrestii*

*Ajuga forrestii* is a perennial herb that can product flowers. It is native to China.

The inventors have discovered that extracts of *Ajuga forrestii* have several biological activities, which can be beneficial to skin. Non-limiting examples of some of these biological activities include antioxidant properties as well as the ability to inhibit TNF-α activity and stimulate or increase collagen I production. Non-limiting examples include its leaves, stems, bark, roots, fruit, flowers or flower buds, seeds, sap, and the entire plant.

51. *Terminalia chebula*

*Terminalia chebula* is a large deciduous tree that can product flowers and fruit. It is native to China, India, Nepal, Sri Lanka, Malaysia, and Vietnam.

The inventors have discovered that extracts of *Terminalia chebula* have several biological activities, which can be beneficial to skin. Non-limiting examples of some of these biological activities include anticoxidant properties and the ability to inhibit TNF-α and tyrosinase activity. Non-limiting examples include its leaves, stems, bark, roots, fruit, flowers or flower buds, seeds, sap, and the entire plant.

52. *Paederia scandens*

*Paederia scandens* is a flowering vine that is native to China.

The inventors have discovered that extracts of *Paederia scandens* have several biological activities, which can be beneficial to skin. Non-limiting examples of some of these biological activities include the ability to inhibit TNF-α and tyrosinase activity. Non-limiting examples include its leaves, stems, bark, roots, fruit, flowers or flower buds, seeds, sap, and the entire plant.

53. *Lonicera japonica*

*Lonicera japonica* is a honeysuckle plant that can produce white and yellow honeysuckles. It is native to Japan.

The inventors have discovered that extracts of *Lonicera japonica* have several biological activities, which can be beneficial to skin. Non-limiting examples of some of these biological activities include antioxidant properties. Non-limiting examples include its leaves, stems, bark, roots, fruit, flowers or flower buds, seeds, sap, and the entire plant.

54. *Achyranthes bidentata*

*Achyranthes bidentata* is a flowering plant that is native to India, Nepal, China, and Japan.

The inventors have discovered that extracts of *Achyranthes bidentata* have several biological activities, which can be beneficial to skin. Non-limiting examples of some of these biological activities include the ability to increase or promote collagen synthesis and the ability to inhibit TNF-α activity. Non-limiting examples include its leaves, stems, bark, roots, fruit, flowers or flower buds, seeds, sap, and the entire plant.

55. *Hedera nepalensis*

*Hedera nepalensis* is a perennial ivy that is native to Nepal, Bhutan, Afghanistan, India, China, Laos, Myanmar, Thailand, and Vietnam.

The inventors have discovered that extracts of *Hedera nepalensis* have several biological activities, which can be beneficial to skin. Non-limiting examples of some of these biological activities include the ability to inhibit TNF-α activity. Non-limiting examples include its leaves, stems, bark, roots, fruit, flowers or flower buds, seeds, sap, and the entire plant.

56. *Canna chinensis*

*Canna chinensis* is a flowering plant that is native to China.

The inventors have discovered that extracts of *Canna chinensis* have several biological activities, which can be beneficial to skin. Non-limiting examples of some of these biological activities include the ability to inhibit TNF-α and tyrosinase activity. Non-limiting examples include its leaves, stems, bark, roots, fruit, flowers or flower buds, seeds, sap, and the entire plant.

57. *Ephedra sinica*

*Ephedra sinica* is a gymnosperm shrub that is native to China.

The inventors have discovered that extracts of *Ephedra sinica* have several biological activities, which can be beneficial to skin. Non-limiting examples of some of these biological activities include antioxidant properties and the ability to inhibit TNF-α and tyrosinase activity. Non-limiting examples include its leaves, stems, bark, roots, fruit, flowers or flower buds, seeds, sap, and the entire plant.

58. *Dichlrocephala auriculata*

*Dichlrocephala auriculata* is a flowering plant that is native to China.

The inventors have discovered that extracts of *Dichlrocephala auriculata* have several biological activities, which can be beneficial to skin. Non-limiting examples of some of these biological activities include the ability to inhibit TNF-α activity. Non-limiting examples include its leaves, stems, bark, roots, fruit, flowers or flower buds, seeds, sap, and the entire plant.

59. *Prunus mume* var. *viridicalyx*

*Prunus mume* var. *viridicalyx* is a tree that is capable of producing white, red, or pinkish flowers. It is native to Japan.

The inventors have discovered that extracts of *Prunus mume* var. *viridicalyx* have several biological activities, which can be beneficial to skin. Non-limiting examples of some of these biological activities include antioxidant properties and the ability to inhibit TNF-α activity. Non-limiting examples include its leaves, stems, bark, roots, fruit, flowers or flower buds, seeds, sap, and the entire plant.

60. *Castanea mollissima*

*Castanea mollissima* is a chestnut tree that is capable of producing flowers and fruits. It is native to China.

The inventors have discovered that extracts of *Castanea mollissima* have several biological activities, which can be beneficial to skin. Non-limiting examples of some of these biological activities include antioxidant properties and the ability to inhibit TNF-α and tyrosinase activity. Non-limiting examples include its leaves, stems, bark, roots, fruit, flowers or flower buds, seeds, sap, and the entire plant.

61. *Elaeagnus bockii*

*Elaeagnus bockii* is a chestnut tree that is capable of producing flowers and fruits. It is native to China.

The inventors have discovered that extracts of *Elaeagnus bockii* have several biological activities, which can be beneficial to skin. Non-limiting examples of some of these biological activities include the ability to inhibit TNF-α activity. Non-limiting examples include its leaves, stems, bark, roots, fruit, flowers or flower buds, seeds, sap, and the entire plant.

62. *Parkia biglobosa*

*Parkia biglobosa* is a large tree with green leaves that is native to Western Africa.

The inventors have discovered that extracts of *Parkia biglobosa* have several biological activities, which can be beneficial to skin. Non-limiting examples of some of these biological activities include the ability to inhibit TNF-α activity. Non-limiting examples include its leaves, stems, bark, roots, fruit, flowers or flower buds, seeds, sap, and the entire plant.

63. *Cinnamomum parthenoxylon*

*Cinnamomum parthenoxylon* is a large tree with green leaves that is native to Cambodia, Indonesia, Malaysia, Philippines, and Vietnam.

The inventors have discovered that extracts of *Cinnamomum parthenoxylon* have several biological activities, which can be beneficial to skin. Non-limiting examples of some of these biological activities include the ability to inhibit TNF-α activity. Non-limiting examples include its leaves, stems, bark, roots, fruit, flowers or flower buds, seeds, sap, and the entire plant.

64. *Cinnamomum parthenoxylon*

*Cinnamomum parthenoxylon* is a large tree with green leaves that is native to Cambodia, Indonesia, Malaysia, Philippines, and Vietnam.

The inventors have discovered that extracts of *Cinnamomum parthenoxylon* have several biological activities, which can be beneficial to skin. Non-limiting examples of some of these biological activities include antioxidant properties and the ability to inhibit TNF-α and tyrosinase activity. Non-limiting examples include its leaves, stems, bark, roots, fruit, flowers or flower buds, seeds, sap, and the entire plant.

65. *Euphorbia esula*

*Euphorbia esula* is a herbaceous perennial plant that is capable of producing yellow flowers. It is native to southern Europe (e.g., England, Netherlands, Germany), China, and Korea.

The inventors have discovered that extracts of *Euphorbia esula* have several biological activities, which can be beneficial to skin. Non-limiting examples of some of these biological activities include antioxidant properties and the ability to inhibit TNF-α and tyrosinase activity. Non-limiting examples include its leaves, stems, bark, roots, fruit, flowers or flower buds, seeds, sap, and the entire plant.

66. *Sauropus androgynus*

*Sauropus androgynus* is a shrub that has green leaves. It is native to China.

The inventors have discovered that extracts of *Sauropus androgynus* have several biological activities, which can be beneficial to skin. Non-limiting examples of some of these biological activities include antioxidant properties and the ability to inhibit melanin production, TNF-α and tyrosinase activity. Non-limiting examples include its leaves, stems, bark, roots, fruit, flowers or flower buds, seeds, sap, and the entire plant.

67. *Chamaecrista mimosoides*

*Chamaecrista mimosoides* is a plant that is capable of producing yellow flowers.

It is native to Asia, Africa, and South Africa.

The inventors have discovered that extracts of *Chamaecrista mimosoides* have several biological activities, which can be beneficial to skin. Non-limiting examples of some of these biological activities include antioxidant properties and the ability to inhibit TNF-α and tyrosinase activity. Non-limiting examples include its leaves, stems, bark, roots, fruit, flowers or flower buds, seeds, sap, and the entire plant.

68. *Crotolaria zanzibarica*

*Crotolaria zanzibarica* is a shrub that can produce yellow flowers. It is native to eastern Africa.

The inventors have discovered that extracts of *Crotolaria zanzibarica* have several biological activities, which can be beneficial to skin. Non-limiting examples of some of these biological activities include the ability to inhibit TNF-α activity. Non-limiting examples include its leaves, stems, bark, roots, fruit, flowers or flower buds, seeds, sap, and the entire plant.

69. *Castanopsis eyrei*

*Castanopsis eyrei* is a shrub that can produce yellow flowers. It is native to eastern Africa.

The inventors have discovered that extracts of *Castanopsis eyrei* have several biological activities, which can be beneficial to skin. Non-limiting examples of some of these biological activities include antioxidant properties and the ability to inhibit TNF-α and tyrosinase activity. Non-limiting examples include its leaves, stems, bark, roots, fruit, flowers or flower buds, seeds, sap, and the entire plant.

70. *Girardinia palmate*

*Girardinia palmate* is a perennial shrub that can produce flowers. It is native to Pakistan.

The inventors have discovered that extracts of *Girardinia palmate* have several biological activities, which can be beneficial to skin. Non-limiting examples of some of these biological activities include the ability to inhibit TNF-α activity. Non-limiting examples include its leaves, stems, bark, roots, fruit, flowers or flower buds, seeds, sap, and the entire plant.

71. *Phoenix roebelenii*

*Phoenix roebelenii* is a palm tree that is native to southeast Asia (e.g., Laos).

The inventors have discovered that extracts of *Phoenix roebelenii* have several biological activities, which can be beneficial to skin. Non-limiting examples of some of these biological activities include antioxidant properties and the ability to inhibit melanin production, TNF-α and tyrosinase activity. Non-limiting examples include its leaves, stems, bark, roots, fruit, flowers or flower buds, seeds, sap, and the entire plant.

72. *Vinca major*

*Vinca major* is a flowering plant native to southern Europe, Spain, and Turkey.

The inventors have discovered that extracts of *Vinca major* have several biological activities, which can be beneficial to skin. Non-limiting examples of some of these biological activities include antioxidant properties and the ability to inhibit melanin production. Non-limiting examples include its leaves, stems, bark, roots, fruit, flowers or flower buds, seeds, sap, and the entire plant.

73. *Swertia macrosperma*

*Swertia macrosperma* is a flowering plant native to China.

The inventors have discovered that extracts of *Swertia macrosperma* have several biological activities, which can be beneficial to skin. Non-limiting examples of some of these biological activities include antioxidant properties and the ability to inhibit melanin production and TNF-α activity. Non-limiting examples include its leaves, stems, bark, roots, fruit, flowers or flower buds, seeds, sap, and the entire plant.

74. *Onosma paniculatum*

*Onosma paniculatum* is a biennial herb that is native to China.

The inventors have discovered that extracts of *Onosma paniculatum* have several biological activities, which can be beneficial to skin. Non-limiting examples of some of these biological activities include the ability to inhibit melanin production and TNF-α activity. Non-limiting examples include its leaves, stems, bark, roots, fruit, flowers or flower buds, seeds, sap, and the entire plant.

75. *Polygonum multiflorum*

*Polygonum multiflorum* is a flowering herb that is native to China.

The inventors have discovered that extracts of *Polygonum multiflorum* have several biological activities, which can be beneficial to skin. Non-limiting examples of some of these biological activities include the ability to inhibit TNF-α activity. Non-limiting examples include its leaves, stems, bark, roots, fruit, flowers or flower buds, seeds, sap, and the entire plant.

76. *Gerbera jamesonii*

*Gerbera jamesonii* is a flowering herb that is native to China.

The inventors have discovered that extracts of *Gerbera jamesonii* have several biological activities, which can be beneficial to skin. Non-limiting examples of some of these biological activities include antioxidant properties and the ability to inhibit melanin production. Non-limiting examples include its leaves, stems, bark, roots, fruit, flowers or flower buds, seeds, sap, and the entire plant. 77. *Astragalus membranaceus*

*Astragalus membranaceus* is a flowering herb that is native to China.

The inventors have discovered that extracts of *Astragalus membranaceus* have several biological activities, which can be beneficial to skin. Non-limiting examples include its leaves, stems, bark, roots, fruit, flowers or flower buds, seeds, sap, and the entire plant.

78. *Duranta repens*

*Duranta repens* is a flowering shrub that is native to Central and South America and the Caribbean.

The inventors have discovered that extracts of *Duranta repens* have several biological activities, which can be beneficial to skin. Non-limiting examples of some of these biological activities include the ability to inhibit TNF-α activity. Non-limiting examples include its leaves, stems, bark, roots, fruit, flowers or flower buds, seeds, sap, and the entire plant.

79. *Callicarpa macrophylla*

*Callicarpa macrophylla* is a flowering plant that produces small white berries. It is native to India.

The inventors have discovered that extracts of *Callicarpa macrophylla* have several biological activities, which can be beneficial to skin. Non-limiting examples of some of these biological activities include antioxidant properties and the ability to inhibit TNF-α activity. Non-limiting examples include its leaves, stems, bark, roots, fruit, flowers or flower buds, seeds, sap, and the entire plant.

80. *Livistona chinensis*

*Livistona chinensis* is a palm tree that is native to China.

The inventors have discovered that extracts of *Livistona chinensis* have several biological activities, which can be beneficial to skin. Non-limiting examples of some of these biological activities include antioxidant properties and the ability to inhibit melanin production and TNF-α activity. Non-limiting examples include its leaves, stems, bark, roots, fruit, flowers or flower buds, seeds, sap, and the entire plant.

81. *Incarvillea arguta*

*Incarvillea arguta* is a flowering plant that produces pinkish flowers. It is native to China and Nepal.

The inventors have discovered that extracts of *Incarvillea arguta* have several biological activities, which can be beneficial to skin. Non-limiting examples of some of these biological activities include the ability to inhibit TNF-α activity. Non-limiting examples include its leaves, stems, bark, roots, fruit, flowers or flower buds, seeds, sap, and the entire plant.

82. *Lepidium virginicum*

*Lepidium virginicum* is a flowering plant that produces white flowers. It is native to North America and Central America.

The inventors have discovered that extracts of *Lepidium virginicum* have several biological activities, which can be beneficial to skin. Non-limiting examples of some of these biological activities include the ability to inhibit TNF-α activity. Non-limiting examples include its leaves, stems, bark, roots, fruit, flowers or flower buds, seeds, sap, and the entire plant.

83. *Fagopyrum cymosum*

*Fagopyrum cymosum* is a flowering plant that produces white flowers. It is native to China.

The inventors have discovered that extracts of *Fagopyrum cymosum* have several biological activities, which can be beneficial to skin. Non-limiting examples of some of these biological activities include antioxidant properties and the ability to inhibit melanin production and TNF-α activity. Non-limiting examples include its leaves, stems, bark, roots, fruit, flowers or flower buds, seeds, sap, and the entire plant.

84. *Quercus rehderiana*

*Quercus rehderiana* is an evergreen tree that is native to China.

The inventors have discovered that extracts of *Quercus rehderiana* have several biological activities, which can be beneficial to skin. Non-limiting examples of some of these biological activities include antioxidant properties and the ability to inhibit TNF-α and tyrosinase activity. Non-limiting examples include its leaves, stems, bark, roots, fruit, flowers or flower buds, seeds, sap, and the entire plant.

85. *Cunninghamia lanceolata*

*Cunninghamia lanceolata* is an evergreen tree that is native to China.

The inventors have discovered that extracts of *Cunninghamia lanceolata* have several biological activities, which can be beneficial to skin. Non-limiting examples of some of these biological activities include antioxidant properties and the ability to inhibit TNF-α activity. Non-limiting examples include its leaves, stems, bark, roots, fruit, flowers or flower buds, seeds, sap, and the entire plant.

86. *Deutzia glomeruliflora*

*Deutzia glomeruliflora* is a flowering shrub that is native to China.

The inventors have discovered that extracts of *Deutzia glomeruliflora* have several biological activities, which can be beneficial to skin. Non-limiting examples of some of these biological activities include antioxidant properties and the ability to inhibit melanin production and TNF-α activity. Non-limiting examples include its leaves, stems, bark, roots, fruit, flowers or flower buds, seeds, sap, and the entire plant.

B. Compositions of the Present Invention

1. Combinations and Amounts of Ingredients

It is contemplated that the compositions of the present invention can include any one of *Oenothera rosea, Salvia plebeian, Alternanthera philoxeroides, Pyrus pyrifolia, Datura stramonium, Picris hieracioides* ssp. *Japonica, Phoebe neurantha, Acanthopanax gracilistylus, Osmanthus fragrans, Michelia chapensis, Rhododendron spinuliferum, Dendrobenthamia capitata, Ficus microcarpa, Vitex negundo, Sequoia sempervirens, Hypericum forrestii, Ficus pumila, Cercis chinensis, Rhododendron decorum, Ficus retusa* ssp. *nitida, Berchemia polyphylla* var. *leioclada, Elaeocarpus decipiens, Quercus variabilis, Prunus serrulata, Melastoma normale, Lycium chinensis, Chamaecyparis pisifera, Millettia dielsiana, Plumbago auriculata, Nandina domestica, Smilax bockii, Schima wallichii, Carissa spinarum, Wisteria floribunda, Schima argentea, Acacia decurrens* var. *dealbata, Viburnum ichangense, Conyza sumatrensis, Lantana camara, Euonymus bungeanus, Loropetalum chinensis* var. *rubrum, Jasminum mesnyi, Stellaria saxatilis, Elscholtzia cypriani, Daucus carota, Bougainvillea glabra, Serissa serissoides, Antidesma acidum, Sargentodoxa cuneata, Ajuga forrestii, Terminalia chebula, Paederia scandens, Lonicera japonica, Achyranthes bidentata, Hedera nepalensis, Canna chinensis, Ephedra sinica, Dichlrocephala auriculata, Prunus mume* var. *viridicalyx, Castanea molissima, Elaeagnus bockii, Parkia biglobosa, cinnamomum parthenoxylon, Euphorbia esula, Sauropus androgynus, Chamaecrista mimosoides, Crotolaria zanzibarica, Castanopsis eyrei, Girardinia palmate, Phoenix roebelenii, Vinca major, Swertia macrosperma, Onosma paniculatum, Polygonum multiflorum, Gerbera jamesonii, Astragalus membranaceus, Duranta repens, Callicarpa macrophylla, Livistona chinensis, Incarvillea arguta, Lepidium virginicum, Fagopyrum cymosum, Quercus rehderiana, Cunninghamia lanceolata,* and/or *Deutzia glomeruliflora* or any combination thereof, or all of such plants, plant parts, or extracts thereof, or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, and/or 85 of such plants, plant parts, or extracts thereof. The compositions can also include additional ingredients described throughout this specification. The concentrations of the plant extracts and/or additional ingredients can vary. In non-limiting embodiments, for example, the compositions can include in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0225%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.5500%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or more, or any range or integer derivable therein, of at least one of the plant extracts identified in this specification or any combination thereof or additional ingredients. In non-limiting aspects, the percentage of such ingredients can be calculated by weight or volume of the total weight of the compositions. The concentrations can vary depending on the desired effect of the compositions or on the product into which the compositions are incorporated.

2. Composition Vehicles

The compositions of the present invention can be formulated into all types of vehicles. Non-limiting examples of suitable vehicles include emulsions (e.g., oil-in-water, water-in-oil, silicone-in-water, water-in-silicone, water-in-oil-in-water, oil-in-water, oil-in-water-in-oil, oil-in-waterin-silicone, etc.), creams, lotions, solutions (both aqueous and hydro-alcoholic), anhydrous bases (such as lipsticks and powders), gels, ointments, pastes, milks, liquids, aerosols, solid forms, or eye jellies. Variations and other appropriate vehicles will be apparent to the skilled artisan and are appropriate for use in the present invention. In certain aspects, the concentrations and combinations of the ingredients can be selected in such a way that the combinations are chemically compatible and do not form complexes which precipitate from the finished product.

It is also contemplated that the plant extracts and additional ingredients identified throughout this specification can be encapsulated for delivery to a target area such as skin. Non-limiting examples of encapsulation techniques include the use of liposomes, vesicles, and/or nanoparticles (e.g., biodegradable and non-biodegradable colloidal particles comprising polymeric materials in which the ingredient is trapped, encapsulated, and/or absorbed—examples include nanospheres and nanocapsules) that can be used as delivery vehicles to deliver such ingredients to skin (see, e.g., U.S. Pat. Nos. 6,387,398; 6,203,802; 5,411,744; Kreuter 1988).

Also contemplated are pharmaceutically-acceptable or pharmacologically-acceptable compositions. The phrase "pharmaceutically-acceptable" or "pharmacologically-acceptable" includes compositions that do not produce an allergic or similar untoward reaction when administered to a human. Typically, such compositions are prepared either as topical compositions, liquid solutions or suspensions, solid forms suitable for solution in, or suspension in, liquid prior to use can also be prepared. Routes of administration can vary with the location and nature of the condition to be treated, and include, e.g., topical, inhalation, intradermal, transdermal, parenteral, intravenous, intramuscular, intranasal, subcutaneous, percutaneous, intratracheal, intraperitoneal, intratumoral, perfusion, lavage, direct injection (e.g., an injectable solution), and oral administration and formulation (e.g., tablets, capsules, etc.).

3. Products

The compositions of the present invention can be incorporated into products. Non-limiting examples of products include cosmetic products, food-based products (e.g., fortified water, energy drinks, nutritional drinks, vitamins, supplements, solid foods), pharmaceutical products, etc. By way of example only, non-limiting cosmetic products include sunscreen products, sunless skin tanning products, hair products (e.g., shampoos, conditioners, colorants, dyes, bleaches, straighteners, and permanent wave products), fingernail products, moisturizing creams, skin creams and lotions, softeners, day lotions, gels, ointments, foundations, night creams, lipsticks and lip balms, cleansers, toners, masks, deodorants, antiperspirants, exfoliating compositions, shaving-related products (e.g., creams, "bracers" and aftershaves), pre-moistened wipes and washcloths, tanning lotions, bath products such as oils, foot care products such as powders and sprays, skin colorant and make-up products such as foundations, blushes, rouges eye shadows and lines, lip colors and mascaras, baby products (e.g., baby lotions, oils, shampoos, powders and wet wipes), and skin or facial peel products. Additionally, the cosmetic products can be formulated as leave-on or rinse-off products.

4. Additional Ingredients

Compositions of the present invention can include additional ingredients. Non-limiting examples of additional ingredients include cosmetic ingredients (both active and non-active) and pharmaceutical ingredients (both active and non-active).

a. Cosmetic Ingredients

The CTFA International Cosmetic Ingredient Dictionary and Handbook (2008), $12^{th}$ Edition, describes a wide variety of non-limiting cosmetic ingredients that can be used in the context of the present invention. Examples of these ingredient classes include: fragrances (artificial and natural), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), adsorbents, emulsifiers, stabilizers, lubricants, solvents, moisturizers (including, e.g., emollients, humectants, film formers, occlusive agents, and agents that affect the natural moisturization mechanisms of the skin), water-repellants, UV absorbers (physical and chemical absorbers such as paraaminobenzoic acid ("PABA") and corresponding PABA derivatives, titanium dioxide, zinc oxide, etc.), essential oils, vitamins (e.g., A, B, C, D, E, and K), trace metals (e.g., zinc, calcium and selenium), anti-irritants (e.g., steroids and non-steroidal anti-inflammatories), botanical extracts (e.g., *Aloe vera*, chamomile, cucumber extract, *Ginkgo biloba*, *ginseng*, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., glycerin, propylene glycol, butylene glycol, pentylene glycol, sorbitol, urea, and manitol), exfoliants (e.g., alpha-hydroxyacids, and beta-hydroxyacids such as lactic acid, glycolic acid, and salicylic acid; and salts thereof) waterproofing agents (e.g., magnesium/aluminum hydroxide stearate), skin conditioning agents (e.g., *Aloe* extracts, allantoin, bisabolol, ceramides, dimethicone, hyaluronic acid, and dipotassium glycyrrhizate), thickening agents (e.g., substances which that can increase the viscosity of a composition such as carboxylic acid polymers, crosslinked polyacrylate polymers, polyacrylamide polymers, polysaccharides, and gums), and silicone containing compounds (e.g., silicone oils and polyorganosiloxanes). The following provides specific non-limiting examples of some of the additional ingredients that can be used with the compositions of the present invention.

i. Sunscreen Agents

UV absorption agents that can be used in combination with the compositions of the present invention include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloy trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bisbenzotriazolyl tetramethylbutyiphenol, and bis-ethylhexyloxyphenol methoxyphenyltriazine, 4-methylbenzylidenecamphor, and isopentyl 4-methoxycinnamate. Non-limiting examples of physical sunblocks include, kaolin, talc, petrolatum and metal oxides (e.g., titanium dioxide and zinc oxide). Compositions of the present invention can have UVA and UVB absorption properties. The compositions can have an sun protection factor (SPF) of 2, 3, 4, 56, 7, 8, 9, 10, 11, 12, 13, 14, 15, 20, 25, 30, 35, 40, 45, 50, 55, 60, 70, 80, 90 or more, or any integer or derivative therein.

ii. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, acrylates/C10-30 alkyl acrylate crosspolymer, acrylates copolymer, alanine, algae extract, *Aloe barbadensis, Aloe-barbadensis* extract, *Aloe barbadensis* gel, *althea officinalis* extract, aluminum starch octenylsuccinate, aluminum stearate, apricot (*Prunus armeniaca*) kernel oil, arginine, arginine aspartate, *Arnica montana* extract, ascorbic acid, ascorbyl palmitate, aspartic acid, avocado (*Persea gratissima*) oil, barium sulfate, barrier sphingolipids, butyl alcohol, beeswax, behenyl alcohol, beta-sitosterol, BHT, birch (*Betula alba*) bark extract, borage (*Borago officinalis*) extract, 2-bromo-2-nitropropane-1,3-diol, butcherbroom (*Ruscus aculeatus*) extract, butylene glycol, *Calendula officinalis* extract, *Calendula officinalis* oil, candelilla (*Euphorbia cerifera*) wax, canola oil, caprylic/capric triglyceride, cardamon (*Elettaria cardamomum*) oil, carnauba (*Copernicia cerifera*) wax, carrageenan (*Chondrus crispus*), carrot (*Daucus carota sativa*) oil, castor (*Ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*Anthemis nobilis*) oil, cholesterol, cholesterol esters, cholesteryl hydroxystearate, citric acid, clary (*Salvia sclarea*) oil, cocoa (*Theobroma cacao*) butter, coco-caprylate/caprate, coconut (*Cocos nucifera*) oil, collagen, collagen amino acids, corn (*Zea mays*) oil, fatty acids, decyl oleate, dextrin, diazolidinyl urea, dimethicone copolyol, dimethiconol, dioctyl adipate, dioctyl succinate, dipentaerythrityl hexacaprylate/hexacaprate, DMDM hydantoin, DNA, erythritol, ethoxydiglycol, ethyl linoleate, *Eucalyptus globulus* oil, evening primrose (*Oenothera biennis*) oil, fatty acids, tructose, gelatin, *Geranium maculatum* oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*Vitis vinifera*) seed oil, hazel (*Corylus americana*) nut oil, hazel (*Corylus avellana*) nut oil, hexylene glycol, honey, hyaluronic acid, hybrid safflower (*Carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, imidazolidinyl urea, iodopropynyl butylcarbamate, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*Jasminum officinale*) oil, jojoba (*Buxus chinensis*) oil, kelp, kukui (*Aleurites moluccana*) nut oil, lactamide MEA, laneth-16, laneth-10 acetate, lanolin, lanolin acid, lanolin alcohol, lanolin oil, lanolin wax, lavender (*Lavandula angustifolia*) oil, lecithin, lemon (*Citrus medica limonum*) oil, linoleic acid, linolenic acid, *Macadamia ternifolia* nut oil, magnesium stearate, magnesium sulfate, maltitol, *Matricaria (Chamomilla recutita)* oil, methyl glucose sesquistearate, methylsilanol PCA, microcrystalline wax, mineral oil, mink oil, *Mortierella* oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*Olea europaea*) oil, orange (*Citrus aurantium dulcis*) oil, palm (*Elaeis guineensis*) oil, palmitic acid, pantethine, panthenol, panthenyl ethyl ether, paraffin, PCA, peach (*Prunus persica*) kernel oil, peanut (*Arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG40 stearate, PEG-50 stearate, PEG-100 stearate, PEG-150 stearate, pentadecalactone, peppermint (*Mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, potassium sorbate, potassium stearate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, quaternium-15, quaternium-18 hectorite, quaternium-22, retinol, retinyl palmitate, rice (*Oryza sativa*) bran oil, RNA, rosemary (*Rosmarinus officinalis*) oil, rose oil, safflower (*Carthamus tinctorius*) oil, sage (*Salvia officinalis*) oil, salicylic acid, sandalwood (*Santalum album*) oil, serine, serum protein, sesame (*Sesamum indicum*) oil, shea butter (*Butyrospermum parkii*), silk powder, sodium chondroitin sulfate, sodium hyaluronate, sodium lactate, sodium palmitate, sodium PCA, sodium polyglutamate, sodium stearate, soluble collagen, sorbic acid, sorbitan laurate, sorbitan oleate, sorbitan palmitate, sorbitan sesquioleate, sorbitan stearate, sorbitol, soybean (*Glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*Helianthus annuus*) seed oil, sweet almond (*Prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*Triticum vulgare*) germ oil, and ylang ylang (*Cananga odorata*) oil.

iii. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCI, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

iv. Structuring Agents

In other non-limiting aspects, the compositions of the present invention can include a structuring agent. Structuring agents, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

v. Emulsifiers

In some non-limiting aspects, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, and mixtures thereof.

vi. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In preferred aspects, the silicon containing compounds includes a silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Mich.

vii. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, *Macadamia* nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, *Eucalyptus* oil, fennel oil, sea fennel oil, frankincense oil, *Geranium* oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

viii. Thickening Agents

Thickening agents, including thickener or gelling agents, include substances that can increase the viscosity of a composition. Thickeners include those that can increase the viscosity of a composition without substantially modifying the efficacy of the active ingredient within the composition. Thickeners can also increase the stability of the compositions of the present invention.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerytritol (e.g., Carbopol™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include *Acacia*, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, *sclerotium* gum, sodium carboyxmethyl dextran, sodium carrageenan, tragacanth gum, xanthan gum, and mixtures thereof.

b. Pharmaceutical Ingredients

Pharmaceutical ingredients are also contemplated as being useful with the emulsion compositions of the present invention. Non-limiting examples of pharmaceutical ingredients include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antpsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

C. Kits

Kits are also contemplated as being used in certain aspects of the present invention. For instance, a composition of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of a composition. In other embodiments, the container can be squeezed (e.g., metal, laminate, or plastic tube) to dispense a desired amount of the composition. The composition can be dispensed as a spray, foam, an aerosol, a liquid, a fluid, or a semi-solid. The containers can have spray, pump, or squeeze mechanisms. A kit can also include instructions for using the kit and/or compositions. Instructions can include an explanation of how to apply, use, and maintain the compositions.

EXAMPLES

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

Materials and Methods for Obtaining Extracts

The extracts identified in Table 1 were prepared from the whole plant. Each plant was individually obtained, ground, and dried, to produce a powder. The powder was treated according to the process described in FIG. 1. Each extract in Table 1 was prepared by and provided to the inventors by Kunming Institute of Botany, Chinese Academy of Sciences, Yunnan, CHINA.

Example 2

Efficacy of Extracts

Each extract prepared according to the process described in Example 1 was subjected to a variety of assays to determine their skin efficacy. The following Table 1 provides a summary of these data. A description of the assays used to obtain these data is provided below Table 1.

TABLE 1

| Plant Extract | B16 Inhibition | Collagen Stimulated | TNF-α Inhibition | AO Activity | Tyrosinase Inhibition |
|---|---|---|---|---|---|
| Oenothera rosea | | | −80.518 | −89.54 | −28.88 |
| Salvia plebeia | | | −42.301 | | −29.22 |
| Elaeagnus lanceolatus | | | −67.626 | −64.13 | −30.22 |
| Docynia delavayi | | | −47.542 | −63.79 | |
| Alternanthera philoxeroides | | | −35.971 | −10.42 | −28.38 |
| Pyrus pyrifolia | | | −20.682 | −87.03 | |
| Datura stramonium | | 61.885 | −44.465 | −26.97 | −24.78 |
| Picris hieracioides ssp. Japonica | | 29.806 | −62.551 | −29.68 | −26.82 |
| Phoebe neurantha | | | −29.541 | −90.49 | −29.37 |
| Acanthopanax gracilistylus | | | −13.25 | −43.66 | −17.62 |
| Osmanthus fragrans | | 35.271 | −65.592 | −74.75 | −21.07 |
| Michelia chapensis | | | −78.229 | −61.21 | −21.2 |
| Rhododendron spinuliferum | | | −81.961 | −91.53 | −39.34 |
| Dendrobenthamia capitata | | | −54.07 | −89.32 | −33.33 |
| Ficus microcarpa | | | −87.697 | −89.96 | −48.02 |
| Vitex negundo | | | | −62.44 | −17.62 |
| Sequoia sempervirens | | | −89.127 | −90.39 | −44.19 |
| Cassia surattensis | | | | −61.48 | |
| Hypericum forrestii | | | | −90.61 | −34.23 |
| Ficus pumila | | | | −45.41 | −27.84 |
| Cercis chinensis | | | | −87.44 | |
| Rhododendron decorum | | | −80.98 | −89.62 | −18.16 |
| Ficus retusa ssp. nitida | | | −82.99 | −81.43 | −18.64 |
| Berchemia polyphylla var. leioclada | | | | −85.34 | −20.79 |
| Elaeocarpus decipiens | | | −85.14 | −90.55 | −25.69 |
| Quercus variabilis | | | −89.098 | −88.76 | −39.43 |
| Prunus serrulata | | | −48.995 | −55.23 | |
| Melastoma normale | | | −89.969 | −90.18 | −42.53 |
| Lycium chinensis | | 64.232 | −23.234 | −71.92 | −24.85 |
| Chamaecyparis pisifera | | | −75.879 | −84.61 | −33.57 |
| Millettia dielsiana | | 63.307 | −55.654 | −80.51 | −24.01 |
| Plumbago auriculata | | | −82.659 | −87.81 | −35.48 |
| Nandina domestica | | | −68.886 | −53.51 | −20.07 |
| Smilax bockii | | | −51.522 | −69.3 | |
| Schima wallichii | | | −85.116 | −90.58 | −49 |
| Thevetia peruviana | | | −66.222 | −24.03 | −19.26 |
| Carissa spinarum | | | −55.148 | −87.7 | — |
| Maesa perlarius | | | −51.022 | −13.7 | −22.58 |
| Wisteria floribunda | | 64.976 | −16.421 | −32.56 | |
| Schima argentea | | | −56.387 | −29.44 | −23.51 |
| Acacia decurrens var. dealbata | | | −94.503 | −89.06 | −36.25 |
| Viburnum ichangense | | 43.022 | −93.66 | −87.08 | −25.37 |
| Conyza sumatrensis | | 60.463 | −65.007 | −21.11 | −22.31 |
| Lantana camara | | | −75.885 | −85.35 | |
| Euonymus bungeanus | | | −73.908 | −72.57 | −26.96 |
| Loropetalum chinensis var. rubrum* | | | −85.4 | −88.38 | −49.8 |
| Jasminum mesnyi | | | −64.987 | −29.23 | −22.58 |
| Stellaria saxatilis | | | −70.043 | | −20.58 |
| Elscholtzia cypriani | | | −86.121 | −38.27 | −17.89 |
| Daucus carota | | | −75.219 | | −22.65 |
| Bougainvillea glabra | | | −55.624 | | −24.45 |
| Serissa serissoides | | | −51.755 | −30.05 | −16.09 |
| Antidesma acidum | | | −88.413 | −84.91 | −45.82 |
| Sargentodoxa cuneata | | | −90.12 | −90.82 | −31.79 |
| Ajuga forrestii* | | | −60.514 | −17.91 | −12.1 |
| Terminalia chebula | | | −88.998 | −91.26 | −38.1 |
| Paederia scandens | | | −64.966 | −27.33 | −22.52 |
| Lonicera japonica | | | −15.155 | −64.62 | −16.22 |
| Achyranthes bidentata | | 48.53 | −66.995 | | −19.05 |
| Hedera nepalensis | | | −58.104 | −23.45 | −18.53 |
| Canna chinensis | | | −76.392 | | −31.02 |
| Ephedra sinica | | | −93.275 | −87.36 | −53.67 |

TABLE 1-continued

| Plant Extract | B16 Inhibition | Collagen Stimulated | TNF-α Inhibition | AO Activity | Tyrosinase Inhibition |
|---|---|---|---|---|---|
| Dichlrocephala auriculata | −21.69 | | −80.436 | −25.39 | −18.65 |
| Prunus mume var. viridicalyx | | | −66.348 | −88.52 | |
| Castanea molissima | | | −74.369 | −89.19 | −33.1 |
| Elaeagnus bockii | | | −62.85 | −34.28 | |
| Parkia biglobosa | | | −46.022 | −54.37 | −15.29 |
| cinnamomum parthenoxlon | | | −83.774 | −88.6 | −23.98 |
| Euphorbia esula | | | −81.957 | −89.55 | −21.18 |
| Sauropus androgynus | −26.05 | | −73.638 | −86.99 | −28.33 |
| Chamaecrista mimosoides | | | −82.346 | −87.57 | −28.47 |
| Crotolaria zanzibarica | | | −83.556 | −29.92 | −13.74 |
| Castanopsis eyrei | | | −87.817 | −87.57 | −28.61 |
| Girardinia palmata | | | −65.887 | | −15.71 |
| Phoenix roebelenii | −22.81 | | −67.826 | −87.57 | −34.78 |
| Vinca major | −23.84 | | −29.153 | −42.35 | |
| Swertia macrosperma | −27.26 | | −77.217 | −53.48 | |
| Onosma paniculatum | −26.25 | | −45.42 | | |
| Polygonum multiflorum | | | −57.213 | | |
| Gerbera jamesonii | −26.28 | | −33.293 | −48.86 | |
| Astragalus membranaceus | | | | | |
| Duranta repens | | | −59.57 | −73.8 | |
| Callicarpa macrophylla | | | −46.109 | −86.99 | |
| Livistona chinensis | −23.15 | | −89.63 | −70.39 | −17.01 |
| Incarvillea arguta | | | −66.723 | −21.13 | |
| Lepidium virginicum | | | −62.833 | −20.37 | −16.23 |
| Fagopyrum cymosum | 28.96 | | −59.044 | −59.26 | |
| Quercus rehderiana | | | −73.343 | −88.65 | −24.29 |
| Cunninghamia lanceolata | | | −91.893 | −84.34 | |
| Deutzia glomeruliflora | −21.36 | | −35.277 | −57.02 | |

**Both *Ajuga forrestii* and *Loropetalum chinensis* extracts were also found to stimulate collagen I synthesis in the skin by the Collagen Stimulation Assay described below B16 Melanogenesis Assay: Melanogenesis is the process by which melanocytes produce melanin, a naturally produced pigment that imparts color to skin, hair, and eyes. Inhibiting melanogenesis is beneficial to prevent skin darkening and lighten dark spots associated with aging. This bioassay utilizes B16-F1 melanocytes (ATCC), an immortalized mouse melanoma cell line, to analyze the effect of compounds on melanogenesis. The endpoint of this assay is a spectrophotometric measurement of melanin production and cellular viability. B16-F1 melanocytes, cultivated in standard DMEM growth medium with 10% fetal bovine serum (Mediatech) at 37° C. in 10% $CO_2$, were treated with each of the extracts identified in Table 1 for 6 days. Following incubation, melanin secretion was measured by absorbance at 405 nm and cellular viability was quantified.

Collagen Stimulation Assay: Collagen is an extracellular matrix protein critical for skin structure. Increased synthesis of collagen helps improve skin firmness and elasticity. This bioassay analyzes the effect of extracts on the production of procollagen peptide (a precursor to collagen) by human epidermal fibroblasts. The endpoint of this assay is a spectrophotometric measurement that reflects the presence of procollagen peptide and cellular viability. The assay employs the quantitative sandwich enzyme immunoassay technique whereby a monoclonal antibody specific for procollagen peptide has been pre-coated onto a microplate. Standards and samples are pipetted into the wells and any procollagen peptide □present is bound by the immobilized antibody. After washing away any unbound substances, an enzyme-linked polyclonal antibody specific for procollagen peptide is added to the wells. Following a wash to remove any unbound antibody-enzyme reagent, a substrate solution is added to the wells and color develops in proportion to the amount of procollagen peptide bound in the initial step using a microplate reader for detection at 450 nm. The color development is stopped and the intensity of the color is measured.

Subconfluent normal human adult epidermal fibroblasts (Cascade Biologics) cultivated in standard DMEM growth medium with 10% fetal bovine serum (Mediatech) at 37° C. in 10% $CO_2$, were treated with each of the extracts identified in Table 1 for 3 days. Following incubation, cell culture medium was collected and the amount of procollagen peptide secretion quantified using a sandwich enzyme linked immuno-sorbant assay (ELISA) from Takara (#MK101).

Tumor Necrosis Factor Alpha (TNF-α) Assay: The prototype ligand of the TNF superfamily, TNF-α, is a pleiotropic cytokine that plays a central role in inflammation. Increase in its expression is associated with an up regulation in pro-inflammatory activity. This bioassay analyzes the effect of extracts on the production of TNF-α by human epidermal keratinocytes. The endpoint of this assay is a spectrophotometric measurement that reflects the presence of TNF-α and cellular viability. The assay employs the quantitative sandwich enzyme immunoassay technique whereby a monoclonal antibody specific for TNF-α has been pre-coated onto a microplate. Standards and samples are pipetted into the wells and any TNF-α □present is bound by the immobilized antibody. After washing away any unbound substances, an enzyme-linked polyclonal antibody specific for TNF-α is added to the wells. Following a wash to remove any unbound antibody-enzyme reagent, a substrate solution is added to the wells and color develops in proportion to the amount of TNF-α bound in the initial step using a microplate reader for detection at 450 nm. The color development is stopped and the intensity of the color is measured.

Subconfluent normal human adult keratinocytes (Cascade Biologics) cultivated in EpiLife standard growth medium (Cascade Biologics) at 37° C. in 5% $CO_2$, were treated with phorbol 12-myristate 13-acetate (PMA, 10 ng/ml, Sigma Chemical, #P1585-1MG) and each of the extracts identified in Table 1 for 6 hours. PMA has been shown to cause a dramatic increase in TNF-α secretion which peaks at 6 hours after treatment. Following incubation, cell culture medium was collected and the amount of TNF-α secretion quantified using a sandwich enzyme linked immuno-sorbant assay (ELISA) from R&D Systems (#DTA00C).

Antioxidant (AO) assay: An in vitro bioassay that measures the total anti-oxidant capacity of an extract. The assay relies on the ability of antioxidants in the sample to inhibit the oxidation of ABTS® (2,2'-azino-di-[3-ethylbenzthiazoline sulphonate]) to ABTS®+ by metmyoglobin. The antioxidant system of living organisms includes enzymes such as superoxide dismutase, catalase, and glutathione peroxidase; macromolecules such as albumin, ceruloplasmin, and ferritin; and an array of small molecules, including ascorbic acid, α-tocopherol, β-carotene, reduced glutathione, uric acid, and bilirubin. The sum of endogenous and food-derived antioxidants represents the total antioxidant activity of the extracellular fluid. Cooperation of all the different antioxidants provides greater protection against attack by reactive oxygen or nitrogen radicals, than any single compound alone. Thus, the overall antioxidant capacity may give more relevant biological information compared to that obtained by the measurement of individual components, as it considers the cumulative effect of all antioxidants present in plasma and body fluids. The capacity of the antioxidants in the sample to prevent ABTS oxidation is compared with that of Trolox, a water-soluble tocopherol analogue, and is quantified as molar Trolox equivalents.

Anti-Oxidant capacity kit #709001 from Cayman Chemical (Ann Arbor, Mich. USA) was used as an in vitro bioassay to measure the total anti-oxidant capacity of each of the extracts identified in Table 1. The protocol was followed according to manufacturer recommendations. The assay relied on antioxidants in the sample to inhibit the oxidation of ABTS® (2,2'-azino-di-[3-ethylbenzthiazoline sulphonate]) to ABTS®.+ by metmyoglobin. The capacity of the antioxidants in the sample to prevent ABTS oxidation was compared with that Trolox, a water-soluble tocopherol analogue, and was quantified as a molar Trolox equivalent.

Tyrosinase activity assay: In mammalian cells, tyrosinase catalyzes two steps in the multi-step biosynthesis of melanin pigments from tyrosine (and from the polymerization of dopachrome). Tyrosinase is localized in melanocytes and produces melanin (aromatic quinone compounds) that imparts color to skin, hair, and eyes.

Purified mushroom tyrosinase (Sigma) was incubated with its substrate L-Dopa (Fisher) in the presence or absence of each of the extracts in Table 1. Pigment formation was evaluated by colorimetric plate reading at 490 nm. The percent inhibition of mushroom tyrosinase activity was calculated compared to non-treated controls to determine the ability of test extracts to inhibit the activity of purified enzyme. Test extract inhibition was compared with that of kojic acid (Sigma).

Example 3

Particular Combinations of Extracts

Based, in part, on the above data, it was discovered that a combination of an aqueous extract from the whole plant of *Polygonum multiflorum* and an aqueous extract from the whole plant (or any part thereof) of *Lonicera japonica* can be used to inhibit/reduce TNF-α activity and inhibit/reduce tyrosinase activity while also providing the skin with protection from the detrimental effects of oxidation. It should be noted that the whole plant was used in these studies, in which such an extract has differing ingredients when compared, for instance, with extracts from a part of the plant such as the leaf, stem, flower, or root. It was also discovered that the addition of an aqueous extract from the whole plant of *Astragalus membranaceus* could be beneficial to skin.

A further discovery was the combination of *Loropetalum chinensis* var. *rubrum* extract from the whole plant with *Ajuga forrestii* extract from the whole plant was found to work especially well to provide skin with protection from oxidative events (e.g., oxidation caused by reaction oxidative species or environmental conditions or sun exposure) as well as inhibit TNF-α activity (which can reduce skin inflammation, calm or soothe skin, and treat erythemic skin), inhibit tyrosinae activity (which can be used to lighten skin, even skin tone, and treat hyperpigmentation, sun spots, or melasma), and increase or activate collagen I synthesis in the skin (which can be used to rebuild the skin matrix, increase collagen within skin, and treat fine lines or wrinkles). It was also discovered that the addition of *Ephedra sinica* extract from the whole plant to this combination can further supplement the inhibition of Tyrosinase activity in skin.

A further discovery was the combination of *Loropetalum chinensis* var. *rubrum* extract from the whole plant with *Ephedra sinica* extract from the whole plant was found to work well together in inhibiting tyrosinase activity in that the combination can produce a synergistic effect.

An even further discovery is that the combination of *Ajuga forrestii* extract from the whole plant with *Ephedra sinica* extract from the whole plant can be used to provide skin with protection from oxidative events (e.g., oxidation caused by reaction oxidative species or environmental conditions or sun exposure) as well as inhibit TNF-α activity (which can reduce skin inflammation, calm or soothe skin, and treat erythemic skin), inhibit tyrosinae activity (which can be used to lighten skin, even skin tone, and treat hyperpigmentation, sun spots, or melasma), and increase or activate collagen synthesis in the skin (which can be used to rebuild the skin matrix, increase collagen within skin, and treat fine lines or wrinkles).

Example 4

Testing Vehicles and Sample Compositions

Tables 2 and 3 describe generic skin testing formulations in which a skin active ingredient can be incorporated into to determine the types of skin benefits that can be attributed to the skin active ingredient. These formulations are prepared in such a manner that any resulting skin benefit from topical application of the formula to skin can be directly attributed to the skin active ingredient being tested. In the context of the present invention, the skin active ingredient that can be tested can be a plant, plant part, or extract thereof from *Oenothera rosea, Salvia* plebeian, *Alternanthera philoxeroides, Pyrus pyrifolia, Datura stramonium, Picris hieracioides* ssp. *Japonica, Phoebe neurantha, Acanthopanax gracilistylus, Osmanthus fragrans, Michelia chapensis, Rhododendron spinuliferum, Dendrobenthamia capitata, Ficus microcarpa, Vitex negundo, Sequoia sempervirens, Hypericum forrestii, Ficus pumila, Cercis chinensis, Rhododendron decorum, Ficus retusa* ssp. *nitida, Berchemia polyphylla* var. *leioclada, Elaeocarpus decipiens, Quercus variabilis, Prunus serrulata, Melastoma normale, Lycium chinensis, Chamaecyparis pisifera, Millettia dielsiana, Plumbago auriculata, Nandina domestica, Smilax bockii, Schima wallichii, Carissa spinarum, Wisteria floribunda, Schima argentea, Acacia decurrens* var. *dealbata, Viburnum ichangense, Conyza sumatrensis, Lantana camara, Euony-* mus bungeanus, Loropetalum chinensis var. rubrum, Jasminum mesnyi, Stellaria saxatilis, Elscholtzia cypriani, Daucus carota, Bougainvillea glabra, Serissa serissoides, Antidesma acidum, Sargentodoxa cuneata, Ajuga forrestii, Terminalia chebula, Paederia scandens, Lonicera japonica, Achyranthes bidentata, Hedera nepalensis, Canna chinensis, Ephedra sinica, Dichlrocephala auriculata, Prunus mume var. viridicalyx, Castanea molissima, Elaeagnus bockii, Parkia biglobosa, cinnamomum parthenoxylon, Euphorbia esula, Sauropus androgynus, Chamaecrista mimosoides, Crotolaria zanzibarica, Castanopsis eyrei, Girardinia palmate, Phoenix roebelenii, Vinca major, Swertia macrosperma, Onosma paniculatum, Polygonum multiforum, Gerbera jamesonii, Astragalus membranaceus, Duranta repens, Callicarpa macrophylla, Livistona chinensis, Incarvillea arguta, Lepidium virginicum, Fagopyrum cymosum, Quercus rehderiana, Cunninghamia lanceolata, and/or Deutzia glomeruliflora or any combination thereof, or all of such plants, plant parts, or extracts thereof, or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, and/or 85 of such plants, plant parts, or extracts thereof. Further, and as noted in Example 3, these particular combinations can be tested in the following vehicles of Tables 2-3. Any portion of the plant extract can be used for testing (e.g., root, stem, leaf, flower, flower bulb, bark, fruit, seed, sap, whole plant etc.). It should be recognized that other standard testing vehicles can also be used to determine the skin benefit properties of extracts obtained from the plant extracts and that the following formulations are non-limiting testing vehicles.

TABLE 2*

| Ingredient | % Concentration (by weight) |
| --- | --- |
| Phase A | |
| Water | 84.80 |
| Xanthum gum | 0.1 |
| M-paraben | 0.15 |
| P-paraben | 0.1 |
| Citric acid | 0.1 |
| Phase B | |
| Cetyl alcohol | 4.0 |
| Glyceryl stearate + PEG 100 | 4.0 |
| Octyl palmitate | 4.0 |
| Dimethicone | 1.0 |
| Tocopheryl acetate | 0.2 |
| Phase C | |
| Plant Extract** | 2.0 |
| TOTAL | 100 |

*Procedure for making composition: Sprinkle Xanthum gum in water and mix for 10 min. Subsequently, add all ingredients in phase A and heat to 70-75° C. Add all items in phase B to separate beaker and heat to 70-75° C. Mix phases A and B at 70-75° C. Continue mixing and allow composition to cool to 30° C. Subsequently, add phase C ingredient while mixing.
**The plant extracts identified throughout this specification can be incorporated into this testing formulation as the skin active ingredient. The extracts can be individually used or combined in this testing vehicle. The concentration ranges of the extract (or combination of extracts) can be modified as desired or needed by increasing or decreasing the amount of water. Any portion of the plant can be used to create the skin-active extract (e.g., root, stem, leaf, flower, flower bulb, bark, fruit, seed, seed pod, sap, whole plant etc.).

TABLE 3*

| Ingredient | % Concentration (by weight) |
| --- | --- |
| Phase A | |
| Water | 78.6 |
| M-paraben | 0.2 |
| P-paraben | 0.1 |
| Na2 EDTA | 0.1 |
| Shea butter | 4.5 |
| Petrolatum | 4.5 |
| Glycerin | 4.0 |
| Propylene Glycol | 2.0 |
| Finsolve TN | 2.0 |
| Phase B | |
| Sepigel 305 | 2.0 |
| Phase C | |
| Plant Extract** | 2.0 |
| TOTAL | 100 |

*Add ingredients in phase A to beaker and heat to 70-75° C. while mixing. Subsequently, add the phase B ingredient with phase A and cool to 30° C. with mixing. Subsequently, add phase C ingredient while mixing.
**The plant extracts identified throughout this specification can be incorporated into this testing formulation as the skin active ingredient. The extracts can be individually used or combined in this testing vehicle. The concentration ranges of the extract (or combination of extracts) can be modified as desired or needed by increasing or decreasing the amount of water. Any portion of the plant can be used to create the skin-active extract (e.g., root, stem, leaf, flower, flower bulb, bark, fruit, seed, seed pod, sap, whole plant etc.).

The formulations represented in Tables 4-9 are non-limiting examples of the types of formulations that can be prepared in the context of the present invention. Any standard method can be used to prepare such formulations. For instance, simple mixing of the ingredients in a beaker can be used. One should mix such ingredients and add heat as necessary to obtain a homogenous composition.

Table 4 includes a non-limiting example of a composition of the present invention. The composition can be formulated into an emulsion (e.g., o/w, w/o, o/w/o, w/o/w, etc.) and the additional ingredients identified throughout the specification can be included into the Table 4 composition (e.g., by adjusting the water content of composition). Further, the concentration ranges of the ingredients identified in Table 6 can vary depending on a desired formulation (e.g., cream, lotion, moisturizer, cleanser, toner, mask, etc.).

TABLE 4

| Ingredient | % Concentration (by weight) |
| --- | --- |
| Water | q.s. |
| Plant Extract* | 0.1% to 10% |
| Glycerin | 3 to 40% |
| Butylene glycol | 0.0001 to 10% |
| Propylene glycol | 0.0001 to 10% |
| Phenoxyethanol | 0.0001 to 10% |
| Disodium EDTA | 0.0001 to 10% |
| Steareth-20 | 0.0001 to 10% |
| Chlorhexidine Diglunonate | 0.0001 to 10% |
| Potassium Sorbate | 0.0001 to 10% |
| Preservative** | 0.0001 to 2% |
| TOTAL | 100 |

*The plant extracts identified throughout this specification can be incorporated into this testing formulation as the skin active ingredient. The extracts can be individually used or combined in this testing vehicle. The concentration ranges of the extract (or combination of extracts) can be modified as desired or needed by increasing or decreasing the amount of water. Any portion of the plant can be used to create the skin-active extract (e.g., root, stem, leaf, flower, flower bulb, bark, fruit, seed, seed pod, sap, whole plant etc.). For instance, the combinations noted in Example 3 can be used.
**Any preservative can be used identified in the specification or those known in the art.

Table 5 includes a non-limiting example of a composition of the present invention. The composition can be formulated into an emulsion (e.g., o/w, w/o, o/w/o, w/o/w, etc.) and the additional ingredients identified throughout the specification can be included into the Table 5 composition (e.g., by adjusting the water content of composition). Further, the concentration ranges of the ingredients identified in Table 5 can vary depending on a desired formulation (e.g., cream, lotion, moisturizer cleanser, etc.).

TABLE 5

| Ingredient | % Concentration (by weight) |
| --- | --- |
| Water | q.s. |
| Plant Extract* | 0.1% to 10% |
| Dimethicone | 0.0001 to 10% |
| Triethanolamine | 0.0001 to 10% |
| Phenonip | 0.0001 to 10% |
| Betaine | 0.0001 to 10% |
| Disodium EDTA | 0.0001 to 10% |
| Tocopheryl acetate | 0.0001 to 10% |
| Prodew 400 | 0.0001 to 10% |
| Preservative** | 0.0001 to 2% |
| TOTAL | 100 |

*The plant extracts identified throughout this specification can be incorporated into this testing formulation as the skin active ingredient. The extracts can be individually used or combined in this testing vehicle. The concentration ranges of the extract (or combination of extracts) can be modified as desired or needed by increasing or decreasing the amount of water. Any portion of the plant can be used to create the skin-active extract (e.g., root, stem, leaf, flower, flower bulb, bark, fruit, seed, seed pod, sap, whole plant etc.). For instance, the combinations noted in Example 3 can be used.
**Any preservative can be used identified in the specification or those known in the art.

Table 6 includes a non-limiting example of a composition of the present invention. The composition can be formulated into an emulsion (e.g., o/w, w/o, o/w/o, w/o/w, etc.) and the additional ingredients identified throughout the specification can be included into the Table 6 composition (e.g., by adjusting the water content of composition). Further, the concentration ranges of the ingredients identified in Table 6 can vary depending on a desired formulation (e.g., cream, lotion, moisturizer cleanser, etc.). In particular embodiments, the Table 8 composition can be a moisturizer.

TABLE 6

| Ingredient | % Concentration (by weight) |
| --- | --- |
| Water | q.s. |
| Plant Extract* | 0.1% to 10% |
| Glycerin | 0.0001 to 10% |
| Pentylene Glycol | 0.0001 to 10% |
| Capryl Glycol | 0.0001 to 10% |
| Disodium EDTA | 0.0001 to 10% |
| Capric/Caprylic Triglyceride | 0.0001 to 10% |
| Lipex 205 (Shea Butter) | 0.0001 to 10% |
| Squalane | 0.0001 to 10% |
| Cetyl Alcohol | 0.0001 to 10% |
| Dimethicone | 0.0001 to 10% |
| Ceramide II | 0.0001 to 10% |
| Stearic Acid | 0.0001 to 10% |
| Super Sterol Ester | 0.0001 to 10% |
| Arlacel 165 | 0.0001 to 10% |
| Simulgel 600 | 0.0001 to 10% |
| TOTAL | 100 |

*The plant extracts identified throughout this specification can be incorporated into this testing formulation as the skin active ingredient. The extracts can be individually used or combined in this testing vehicle. The concentration ranges of the extract (or combination of extracts) can be modified as desired or needed by increasing or decreasing the amount of water. Any portion of the plant can be used to create the skin-active extract (e.g., root, stem, leaf, flower, flower bulb, bark, fruit, seed, seed pod, sap, whole plant etc.). For instance, the combinations noted in Example 3 can be used.

Table 7 includes a non-limiting example of a composition of the present invention. The composition can be formulated into an emulsion (e.g., o/w, w/o, o/w/o, w/o/w, etc.) and the additional ingredients identified throughout the specification can be included into the Table 7 composition (e.g., by adjusting the water content of composition). Further, the concentration ranges of the ingredients identified in Table 7 can vary depending on a desired formulation (e.g., cream, lotion, moisturizer cleanser, etc.). In particular embodiments, the Table 9 composition can be a moisturizer.

TABLE 7

| Ingredient | % Concentration (by weight) |
| --- | --- |
| Water | q.s. |
| Plant Extract* | 0.1% to 10% |
| Glycerin | 0.0001 to 10% |
| Pentylene Glycol | 0.0001 to 10% |
| Capryl Glycol | 0.0001 to 10% |
| Disodium EDTA | 0.0001 to 10% |
| Petrolatum | 0.0001 to 10% |
| Squalane | 0.0001 to 10% |
| Cetyl Alcohol | 0.0001 to 10% |
| Arlacel 165 | 0.0001 to 10% |
| Dimethicone | 0.0001 to 10% |
| Simulgel 600 | 0.0001 to 10% |
| TOTAL | 100 |

*The plant extracts identified throughout this specification can be incorporated into this testing formulation as the skin active ingredient. The extracts can be individually used or combined in this testing vehicle. The concentration ranges of the extract (or combination of extracts) can be modified as desired or needed by increasing or decreasing the amount of water. Any portion of the plant can be used to create the skin-active extract (e.g., root, stem, leaf, flower, flower bulb, bark, fruit, seed, seed pod, sap, whole plant etc.). For instance, the combinations noted in Example 3 can be used.

Table 8 includes a non-limiting example of a composition of the present invention. The composition can be formulated into an emulsion (e.g., o/w, w/o, o/w/o, w/o/w, etc.) and the additional ingredients identified throughout the specification can be included into the Table 8 composition (e.g., by adjusting the water content of composition). Further, the concentration ranges of the ingredients identified in Table 8 can vary depending on a desired formulation (e.g., cream, lotion, moisturizer cleanser, etc.). In particular embodiments, the Table 8 composition can be a sunscreen lotion.

TABLE 8

| Ingredient | % Concentration (by weight) |
| --- | --- |
| Water | q.s. |
| Plant Extract* | 0.1% to 10% |
| Xanthan Gum | 0.0001 to 10% |
| Disodium EDTA | 0.0001 to 10% |
| Pentylene Glycol | 0.0001 to 10% |
| Capryl Glycol | 0.0001 to 10% |
| Pemulen TR-1 | 0.0001 to 10% |
| Triethanolamine | 0.0001 to 10% |
| PVP/Hexadecene Copolymer | 0.0001 to 10% |
| Finsolv TN | 10 to 30% |
| Sorbitan Isostearate | 0.0001 to 10% |
| Sunscreen Ingredient** | 2 to 25% |
| TOTAL | 100 |

*The plant extracts identified throughout this specification can be incorporated into this testing formulation as the skin active ingredient. The extracts can be individually used or combined in this testing vehicle. The concentration ranges of the extract (or combination of extracts) can be modified as desired or needed by increasing or decreasing the amount of water. Any portion of the plant can be used to create the skin-active extract (e.g., root, stem, leaf, flower, flower bulb, bark, fruit, seed, seed pod, sap, whole plant etc.). For instance, the combinations noted in Example 3 can be used.
**Sunscreen ingredient can be any sunscreen ingredient, or combination of such ingredients, identified in the specification or known to those of ordinary skill in the art. In one embodiment, the sunscreen ingredient is a combination of zinc oxide and titanium dioxide.

Table 9 includes a non-limiting example of a composition of the present invention. The additional ingredients identified throughout the specification can be included into the Table 9 composition (e.g., by adjusting the water content of composition). Further, the concentration ranges of the ingredients identified in Table 9 can vary depending on a desired formulation (e.g., cream, lotion, moisturizer cleanser, etc.). In particular embodiments, the Table 9 composition can be a cleanser.

TABLE 9

| Ingredient | % Concentration (by weight) |
| --- | --- |
| Water | q.s. |
| Plant Extract* | 0.1% to 10% |
| Disodium EDTA | 0.0001 to 10% |
| Citric Acid | 0.0001 to 10% |
| Pentylene Glycol | 0.0001 to 10% |
| Capryl Glycol | 0.0001 to 10% |
| sodium methyl cocoyl taurate | 10 to 30% |
| sodium cocoamphodiacetate | 1 to 10% |
| TOTAL | 100 |

*The plant extracts identified throughout this specification can be incorporated into this testing formulation as the skin active ingredient. The extracts can be individually used or combined in this testing vehicle. The concentration ranges of the extract (or combination of extracts) can be modified as desired or needed by increasing or decreasing the amount of water. Any portion of the plant can be used to create the skin-active extract (e.g., root, stem, leaf, flower, flower bulb, bark, fruit, seed, seed pod, sap, whole plant etc.). For instance, the combinations noted in Example 3 can be used.

Example 5

Assays that can be Used to Test Compositions

The efficacy of compositions comprising the plant extracts identified throughout the specification, or a combination of such extracts (including, for example, the formulations identified in Tables 2-9), can be determined by methods known to those of ordinary skill in the art. The following are non-limiting assays that can be used in the context of the present invention. It should be recognized that other testing procedures can be used, including, for example, objective and subjective procedures.

Erythema Assay: An assay to measure the reduction of skin redness can be evaluated using a Minolta Chromometer. Skin erythema may be induced by applying a 0.2% solution of sodium dodecyl sulfate on the forearm of a subject. The area is protected by an occlusive patch for 24 hrs. After 24 hrs, the patch is removed and the irritation-induced redness can be assessed using the a* values of the Minolta Chroma Meter. The a* value measures changes in skin color in the red region. Immediately after reading, the area is treated with a formula containing any one, or any combination thereof, of the extracts identified throughout the specification. In particular aspects, the extract can be a *Camptotheca acuminate* extract, a *Loropetalum chinensis* extract, a *Chrysalidocarpus lutscens* extract, or a *Potamogenton perforliatus* extract, or any combination thereof. Repeat measurements are taken at regular intervals to determine the formula's ability to reduce redness, inflammation, or skin irritation.

Skin Moisture/Hydration Assay: Skin moisture/hydration benefits can be measured by using impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. The unit can be calibrated according to instrument instructions for each testing day. A notation of temperature and relative humidity can also be made. Subjects can be evaluated as follows: prior to measurement they can equilibrate in a room with defined humidity (e.g., 30-50%) and temperature (e.g., 68-72° C.). Three separate impedance readings can be taken on each side of the face, recorded, and averaged. The T5 setting can be used on the impedance meter which averages the impedance values of every five seconds application to the face. Changes can be reported with statistical variance and significance.

Skin Clarity and Reduction in Freckles and Age Spots Assay: Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether a composition is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as $(a^2+b2)^{1/2}$.

Skin Dryness, Surface Fine Lines, Skin Smoothness, and Skin Tone Assay: Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical Grading of Skin Tone Assay: Clinical grading of skin tone can be performed via a ten point analog numerical scale: (10) even skin of uniform, pinkish brown color. No dark, erythremic, or scaly patches upon examination with a hand held magnifying lens. Microtexture of the skin very uniform upon touch; (7) even skin tone observed without magnification. No scaly areas, but slight discolorations either due to pigmentation or erythema. No discolorations more than 1 cm in diameter; (4) both skin discoloration and uneven texture easily noticeable. Slight scaliness. Skin rough to the touch in some areas; and (1) uneven skin coloration and texture. Numerous areas of scaliness and discoloration, either hypopigmented, erythremic or dark spots. Large areas of uneven color more than 1 cm in diameter. Evaluations were made independently by two clinicians and averaged.

Clinical Grading of Skin Smoothness Assay: Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations were made independently by two clinicians and averaged.

Skin Smoothness and Wrinkle Reduction Assay With Methods Disclosed in Packman et al. (1978): Skin smoothness and wrinkle reduction can also be assessed visually by using the methods disclosed in Packman et al. (1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Skin Firmness Assay with a Hargens Ballistometer: Skin firmness can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin Softness/Suppleness Assay with a Gas Bearing Electrodynamometer: Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

Appearance of Lines and Wrinkles Assay with Replicas: The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subjects' face and analyzing the replicas image using a computer image analysis system. Replicas can be taken from the eye area and the neck area, and photographed with a digital camera using a low angle incidence lighting. The digital images can be analyzed with an image processing program and the are of the replicas covered by wrinkles or fine lines was determined.

Surface Contour of the Skin Assay with a Profilometer/Stylus Method: The surface contour of the skin can be measured by using the profilometer/Stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fix axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt which is the maximum vertical distance between the highest peak and lowest trough, and Rz which is the mean peak amplitude minus the mean peak height. Values are given as a calibrated value in mm. Equipment should be standardized prior to each use by scanning metal standards of know values. Ra Value can be computed by the following equation: $R_a$=Standardize roughness; $l_m$=the traverse (scan) length; and y=the absolute value of the location of the profile relative to the mean profile height (x-axis).

MELANODERM™ Assay: In other non-limiting aspects, the efficacy of the compositions of the present invention can be evaluated by using a skin analog, such as, for example, MELANODERM™. Melanocytes, one of the cells in the skin analog, stain positively when exposed to L-dihydroxyphenyl alanine (L-DOPA), a precursor of melanin. The skin analog, MELANODERM™, can be treated with a variety of bases containing the compositions and whitening agents of the present invention or with the base alone as a control. Alternatively, an untreated sample of the skin analog can be used as a control.

ORAC Assay: Oxygen Radical Absorption (or Absorbance) Capacity (ORAC) of the aromatic skin-active ingredients and compositions can also be assayed by measuring the antioxidant activity of such ingredients or compositions. This assay can quantify the degree and length of time it takes to inhibit the action of an oxidizing agent such as oxygen radicals that are known to cause damage cells (e.g., skin cells). The ORAC value of the aromatic skin-active ingredients and compositions can be determined by methods known to those of ordinary skill in the art (see U.S. Publication Nos. 2004/0109905 and 2005/0163880; Cao et al. (1993)), all of which are incorporated by reference). In summary, the assay described in Cao et al. (1993) measures the ability of antioxidant compounds in test materials to inhibit the decline of B-phycoerythrm (B-PE) fluorescence that is induced by a peroxyl radical generator, AAPH.

Elastase Assay: EnzChek® Elastase Assay (Kit #E-12056) from Molecular Probes (Eugene, Oreg. USA) can be used as an in vitro enzyme inhibition assay for measuring inhibition of elastase activity for each of the plants, plant parts, and/or extracts thereof disclosed in this specification. The EnzChek kit contains soluble bovine neck ligament elastin that has been labeled with dye such that the conjugate's fluorescence is quenched. The non-fluorescent substrate can be digested by elastase or other proteases to yield highly fluorescent fragments. The resulting increase in fluorescence can be monitored with a fluorescence microplate reader. Digestion products from the elastin substrate have absorption maxima at ~505 nm and fluorescence emission maxima at ~515 nm. The peptide, chloromethyl ketone, is used as a selective, collective inhibitor of elastase when utilizing the EnzChek Elastase Assay Kit for screening for elastase inhibitors.

Lipoxygenase (LO) Assay: An in vitro lipoxygenase (LO) inhibition assay. LOs are non-heme iron-containing dioxygenases that catalyze the addition of molecular oxygen to fatty acids. Linoleate and arachidonate are the main substrates for LOs in plants and animals. Arachadonic acid may then be converted to hydroxyeicosotrienenoic (HETE) acid derivatives, that are subsequently converted to leukotirenes, potent inflammatory mediators. This assay provides an accurate and convenient method for screening lipoxygenase inhibitors by measuring the hydroperoxides generated from the incubation of a lipoxygenase (5-, 12-, or 15-LO) with arachidonic acid.

The Colorimetric LO Inhibitor screening kit (#760700, Cayman Chemical) can be used to determine the ability of each of the plants, plant parts, and/or extracts thereof disclosed in this specification to inhibit enzyme activity. Purified 15-lipoxygenase and test extracts can be mixed in assay buffer and incubated with shaking for 10 min at room temperature. Following incubation, arachidonic acid can be added to initiate the reaction and mixtures incubated for an additional 10 min at room temperature. Colorimetric substrate can be added to terminate catalysis and color progression can be evaluated by fluorescence plate reading at 490 nm. The percent inhibition of lipoxyganse activity can be calculated compared to non-treated controls to determine the ability of test extracts to inhibit the activity of purified enzyme.

Cyclooxygenase (COX) Assay: An in vitro cyclooxygenase-1 and -2 (COX-1, -2) inhibition assay. COX is a bifunctional enzyme exhibiting both cyclooxygenase and peroxidase activities. The cyclooxygenase activity converts arachidonic acid to a hydroperoxy endoperoxide (Prostaglandin G2; PGG2) and the peroxidase component reduces the endoperoxide (Prostaglandin H2; PGH2) to the corresponding alcohol, the precursor of prostaglandins, thromboxanes, and prostacyclins. This COX Inhibitor screening assay measures the peroxidase component of cyclooxygenases. The peroxidase activity is assayed colorimetrically by monitoring the appearance of oxidized N,N,N',N'-tetramethyl-p-phenylenediamine (TMPD). This inhibitor screening assay includes both COX-1 and COX-2 enzymes in order to screen isozyme-specific inhibitors.

The Colormetric COX (ovine) Inhibitor screening assay (#760111, Cayman Chemical), can be used to analyze the effects of each of the plants, plant parts, and/or extracts thereof disclosed in this specification on the activity of purified cyclooxygnase enzyme (COX-1 or COX-2). According to manufacturer instructions, purified enzyme, heme and test extracts can be mixed in assay buffer and incubated with shaking for 15 min at room temperature. Following incubation, arachidonic acid and colorimetric substrate can be added to initiate the reaction. Color progression can be evaluated by colorimetric plate reading at 590 nm. The percent inhibition of COX-1 or COX-2 activity can be calculated compared to non-treated controls to determine the ability of test extracts to inhibit the activity of purified enzyme.

Matrix Metalloproteinase Enzyme Activity (MMP1) Assay: An in vitro matrix metalloprotease (MMP) inhibition assay. MMPs are extracellular proteases that play a role in many normal and disease states by virtue of their broad substrate specificity. MMP1 substrates include collagen IV. The Molecular Probes Enz/Chek Gelatinase/Collagenase Assay kit (#E12055) utilizes a fluorogenic gelatin substrate to detect MMP1 protease activity. Upon proteolytic cleavage, bright green fluorescence is revealed and may be monitored using a fluorescent microplate reader to measure enzymatic activity.

The Enz/Chek Gelatinase/Collagenase Assay kit (#E12055) from Invitrogen can be used as an in vitro assay to measure MMP1 enzymatic activity for each of the plants, plant parts, and/or extracts thereof disclosed in this specification. The assay relies upon the ability of purified MMP1 enzyme to degrade a fluorogenic gelatin substrate. Once the substrate is specifically cleaved by MMP1 bright green fluorescence is revealed and may be monitored using a fluorescent microplate reader. Test materials can be incubated in the presence or absence of the purified enzyme and substrate to determine their protease inhibitor capacity.

Matrix Metalloproteinase Enzyme Activity 3 (MMP3) assay: An in vitro matrix metalloprotease (MMP) inhibition assay can be used for each of the plants, plant parts, and/or extracts thereof disclosed in this specification. MMPs are extracellular proteases that play a role in many normal and disease states by virtue of their broad substrate specificity. MMP3 substrates include collagens, fibronectins, and laminin. Using Colorimetric Drug Discovery kits from BioMol International for MMP3 (AK-400), this assay is designed to measure protease activity of MMPs using a thiopeptide as a chromogenic substrate (Ac-PLG42-mercapto-4-methyl-pentanoylRG-OC2H5)5,6. The MMP cleavage site peptide bond is replaced by a thioester bond in the thiopeptide. Hydrolysis of this bond by an MMP produces a sulfhydryl group, which reacts with DTNB [5,5'-dithiobis(2-nitrobenzoic acid), Ellman's reagent] to form 2-nitro-5-thiobenzoic acid, which can be detected by its absorbance at 412 nm ($\varepsilon$=13,600 M-1 cm-1 at pH 6.0 and above 7).

All of the skin-active ingredients, compositions, or methods disclosed and claimed in this specification can be made and executed without undue experimentation in light of the present disclosure. While the skin-active ingredients, compositions, or methods of this invention have been described in terms of particular embodiments, it will be apparent to those of skill in the art that variations may be applied to the skin-active ingredients, compositions, or methods and in the steps or in the sequence of steps of the method described herein without departing from the concept, spirit and scope of the invention.

The invention claimed is:

1. A method for treating skin of a person in need thereof, the method comprising topically applying to the skin of the person a composition comprising an effective amount of an aqueous, alcoholic, or aqueous-alcoholic leaf extract from *Sequoia sempervirens*, *Geranium* oil, panthenol, citric acid, and glycerin, wherein the composition increases antioxidant activity in the skin and/or increases skin moisture content.

2. The method of claim 1, wherein the composition reduces oxidative damage to skin.

3. The method of claim 1, wherein the composition is applied to dehydrated skin.

4. The method of claim 3, wherein the dehydrated is dry skin.

5. The method of claim 3, wherein the composition increases skin moisture content.

6. The method of claim 1, wherein the composition is applied to sagging or loose skin.

7. The method of claim 6, wherein the composition increases skin elasticity or firmness.

8. The method of claim 1, wherein the composition is applied to a fine line or wrinkle.

9. The method of claim 1, wherein the composition is an emulsion.

10. The method of claim 9, wherein the composition is an oil-in-water emulsion.

11. The method of claim 1, wherein the composition is a cream or a lotion.

12. The method of claim 1, wherein the composition is a solution.

13. The method of claim 1, wherein the composition comprises 0.001% to 5%, by weight, of the extract.

14. The method of claim 1, wherein the composition further comprises:
 (a) grapefruit oil;
 (b) orange oil;
 (c) cedar oil;
 (d) *Eucalyptus* oil;
 (e) rosemary oil;
 (f) peppermint oil.

15. The method of claim 14, wherein the composition further comprises:
 (a) carbomer;
 (b) guar hydroxypropyltrimonium chloride;
 (c) ethylhexylglycerin;
 (d) sodium hydroxide; and
 (e) phenoxyethanol.

16. The method of claim 1, wherein the composition further comprises:
 (a) *Aloe*;
 (b) patchouli oil;
 (c) bergamot oil;
 (d) lavender oil;
 (e) vetiver oil;
 (f) xanthan gum; and
 (g) sorbic acid.

17. The method of claim 1, where the composition further comprises:
 (a) water;
 (b) a chelating agent;
 (c) a moisturizing agent;
 (d) a preservative; and
 (e) a thickening agent.

18. The method of claim 1, wherein the extract is in liquid form and comprises the extracting solvent.

19. The method of claim 1, wherein the extract is a lyophilized extract in powdered form.

20. The method of claim 1, wherein the extract is from the whole plant of *Sequoia sempervirens*.

21. The method of claim 1, wherein the extract is an alcoholic extract.

22. The method of claim 21, wherein the alcoholic extract is an ethanolic extract.

\* \* \* \* \*